(12) United States Patent
Chin

(10) Patent No.: US 9,872,694 B2
(45) Date of Patent: Jan. 23, 2018

(54) TISSUE REMOVAL SYSTEM

(75) Inventor: Albert Chun-Chi Chin, Newton, MA (US)

(73) Assignee: HOLOGIC, INC., Marlborough, MA (US)

(*) Notice: Subject to any disclaimer, the term of this patent is extended or adjusted under 35 U.S.C. 154(b) by 0 days.

(21) Appl. No.: 13/344,545

(22) Filed: Jan. 5, 2012

(65) Prior Publication Data
US 2012/0172889 A1 Jul. 5, 2012

Related U.S. Application Data

(60) Provisional application No. 61/430,144, filed on Jan. 5, 2011.

(51) Int. Cl.
| | |
|---|---|
| *A61B 17/32* | (2006.01) |
| *A61B 17/42* | (2006.01) |
| *A61B 17/00* | (2006.01) |

(52) U.S. Cl.
CPC ........ *A61B 17/32002* (2013.01); *A61B 17/42* (2013.01); *A61B 2017/00017* (2013.01);
(Continued)

(58) Field of Classification Search
CPC ............ A61B 10/02; A61B 2010/0208; A61B 10/0266; A61B 10/0275; A61B 10/0283; A61B 10/0291; A61B 10/0233; A61B 10/0241; A61B 10/025; A61B 2017/00017; A61B 17/285; A61B 17/295;
(Continued)

(56) References Cited

U.S. PATENT DOCUMENTS

| | | | |
|---|---|---|---|
| 4,940,061 A | * | 7/1990 | Terwilliger et al. .......... 600/567 |
| 5,602,449 A | | 2/1997 | Krause et al. |

(Continued)

FOREIGN PATENT DOCUMENTS

| | | |
|---|---|---|
| WO | 99/11184 | 3/1999 |
| WO | WO 00/22994 A1 | 4/2000 |

OTHER PUBLICATIONS

PCT International Search Report for PCT/US2012/020376, Applicant: Hologic, Inc., Form PCT/ISA/210 and 220, dated Jul. 2, 2012 (5pages).

(Continued)

*Primary Examiner* — David C Eastwood
(74) *Attorney, Agent, or Firm* — Vista IP Law Group, LLP

(57) ABSTRACT

A tissue removal system includes an inner tubular member configured to rotate and oscillate axially relative to an outer tubular member, and a reversible motor comprising a rotatable output shaft operatively coupled to the inner tubular member. A proximal end of the inner tubular member is disposed within, and configured to rotate and oscillate axially relative to, a housing. A first control switch disposed within the housing is actuated when the inner tubular member is in a distal position relative to the housing, and a second control switch disposed external to the housing is actuated by a user. The system further includes motor control circuitry configured such that when the second control switch is actuated, actuation of the first control switch causes the motor output shaft to change direction, and when the second control switch is not actuated, actuation of the first control switch causes the motor to turn off.

17 Claims, 11 Drawing Sheets

(52) U.S. Cl.
CPC .............. *A61B 2017/320024* (2013.01); *A61B 2017/320028* (2013.01); *A61B 2017/4216* (2013.01); *A61B 2217/005* (2013.01); *A61B 2217/007* (2013.01)

(58) Field of Classification Search
CPC .............. A61B 17/32; A61B 17/32002; A61B 2017/00398; A61B 2017/320024; A61B 2017/32004; A61B 2017/320044; A61B 2017/320028; A61B 17/42; A61B 2017/4216; A61B 17/46
USPC ......... 600/560–568; 606/119, 120, 125, 126, 606/127–128, 167, 170, 171, 174, 180; 604/30–35, 22, 67, 19, 27, 40–45, 65–66, 604/118–121, 503, 540–543
See application file for complete search history.

(56) References Cited

U.S. PATENT DOCUMENTS

| | | | |
|---|---|---|---|
| 5,730,752 A | 3/1998 | Alden et al. | |
| 5,906,615 A | 5/1999 | Thompson | |
| 6,032,673 A | 3/2000 | Savage et al. | |
| 6,120,462 A * | 9/2000 | Hibner et al. | 600/566 |
| 6,245,084 B1 | 6/2001 | Mark et al. | |
| 6,428,487 B1 * | 8/2002 | Burdorff et al. | 600/568 |
| 7,226,459 B2 | 6/2007 | Cesarini et al. | |
| 2001/0011156 A1 * | 8/2001 | Viola et al. | 600/568 |
| 2001/0047183 A1 * | 11/2001 | Privitera et al. | 606/170 |
| 2002/0026126 A1 * | 2/2002 | Burdorff et al. | 600/564 |
| 2004/0249307 A1 * | 12/2004 | Thompson et al. | 600/568 |
| 2006/0047185 A1 | 3/2006 | Shener et al. | |
| 2009/0270812 A1 | 10/2009 | Litscher et al. | |
| 2009/0270898 A1 * | 10/2009 | Chin et al. | 606/170 |
| 2010/0152762 A1 | 6/2010 | Mark | |

OTHER PUBLICATIONS

PCT Written Opinion of the International Search Authority for PCT/US2012/020376, Applicant: Hologic, Inc., Form PCT/ISA/237, dated Jul. 2, 2012 (6pages).

* cited by examiner

TISSUE REMOVAL SYSTEM

RELATED APPLICATION DATA

The present application claims the benefit under 35 U.S.C. § 119 to U.S. Provisional Application No. 61/430,144, filed Jan. 5, 2011, the contents of which are fully incorporated herein by reference.

BACKGROUND

Field

The present inventions relate to surgical tissue morcellators in which a cutter blade is both rotated and translated during operation.

Description of the Related Art

There are many situations in which it is desirable to remove unwanted tissue from a patient. Uterine fibroids and uterine polyps represent two such types of unwanted tissue. Uterine fibroids are well-defined, non-cancerous tumors that are commonly found in the smooth muscle layer of the uterus. Uterine polyps are wispy masses that are commonly found extending from the inner lining of the uterus. In many instances, uterine fibroids and uterine polyps can grow to be several centimeters in diameter and may cause symptoms like menorrhagia (prolonged or heavy menstrual bleeding), pelvic pressure or pain, and reproductive dysfunction. It is believed that uterine fibroids occur in a substantial percentage of the female population, perhaps in at least 20 to 40 percent of all women, and that uterine polyps occur in up to 10 percent of all women.

One type of treatment for uterine fibroids and uterine polyps is hysteroscopic resection. Hysteroscopic resection typically involves inserting a hysteroscope (i.e., an imaging scope) into the uterus through the vagina, i.e., transcervically, and then cutting away the unwanted tissue from the uterus using a device delivered to the unwanted tissue by the hysteroscope. Hysteroscopic resections typically fall into one of two varieties. In one variety, an electrocautery device in the form of a loop-shaped cutting wire is fixedly mounted on the distal end of the hysteroscope—the combination of the hysteroscope and the electrocautery device typically referred to as a resectoscope. The transmission of electrical current to the uterus with a resectoscope is typically monopolar, and the circuit is completed by a conductive path to the power unit for the device through a conductive pad applied to the patient's skin. In this manner, tissue is removed by contacting the loop with the part of the uterus wall of interest. Examples of such devices are disclosed, for example, in U.S. Pat. No. 5,906,615, inventor Thompson, issued May 25, 1999.

In the other variety of hysteroscopic resection, an electromechanical cutter is inserted through a working channel in the hysteroscope. The electromechanical cutter typically includes (i) a tubular member having a window through which tissue may enter and (ii) a cutting instrument positioned within the tubular member for cutting the tissue that has entered the tubular member through the window. In use, the cutter is positioned near the part of the uterus wall of interest. Tissue is then drawn, typically by suction, into the window, and then the tissue drawn into the window is cut with the cutting instrument. Examples of the electromechanical cutter variety of hysteroscopic resection are disclosed in, for example, U.S. Pat. No. 7,226,459, inventors Cesarini et al., issued Jun. 5, 2007; U.S. Pat. No. 6,032,673, inventors Savage et al., issued Mar. 7, 2000; U.S. Pat. No. 5,730,752, inventors Alden et al., issued Mar. 24, 1998; U.S. Patent Application Publication No. US 2009/0270898 A1, inventors Chin et al., published Oct. 29, 2009; U.S. Patent Application Publication No. US 2009/0270812 A1, inventors Litscher et al., published Oct. 29, 2009; U.S. Patent Application Publication No. US 2006/0047185 A1, inventors Shener et al., published Mar. 2, 2006; and PCT International Publication No. WO 99/11184, published Mar. 11, 1999, all of which are incorporated herein by reference.

SUMMARY OF THE INVENTION

The presently disclosed inventions are directed to hysteroscopic tissue removal systems that may be used, without limitation, for removing uterine fibroids and other gynecological tissues.

A tissue removal system disclosed herein includes an outer tubular member having a closed distal end and a resection window proximal to the distal end; an inner tubular member disposed within the outer tubular member, the inner tubular member comprising a longitudinal axis and a distal end, wherein the distal end of the inner tubular member is movable across the resection window for cutting tissue extending through the resection window; a rotational drive shaft coupled to the inner tubular member and configured for rotating the inner tubular member about the longitudinal axis; a translational drive shaft coupled to the inner tubular member configured for axially oscillating the inner tubular member such that the distal end of the inner tubular member moves back and forth across the resection window; a rotational motor operatively coupled to the rotational drive shaft; and a translational motor operatively coupled to the translational drive shaft such that the rotational motor and the translational motor are independently operable.

In some embodiments, the translational motor may be reversible to rotate a worm gear both clock-wise and counter clock-wise, wherein rotation of the worm gear causes the translational drive shaft to axially oscillate.

The tissue removal system may further include a housing coupled to a proximal end of the outer tubular member, wherein a proximal end of the inner tubular member extends inside the housing, and wherein a proximal end of the housing defines a first lumen through which the rotational drive shaft is received, and a second lumen through which the translational drive shaft is received.

The tissue removal system may further include a rotational gear fixedly coupled to a distal end of the rotational drive shaft; and a driven gear fixedly coupled to a proximal end of the inner tubular member, wherein the rotational gear engages the driven gear, such that rotation of the rotational drive shaft causes rotation of the inner tubular member. The driven gear may be sufficiently elongated such that the driven gear and the rotational gear remain engaged as the driven gear translates axially relative to the rotational gear.

The tissue removal system may further include a saddle member fixedly coupled to a distal end of the translational drive shaft such that axial translation of the translational drive shaft causes axial translation of the saddle member, wherein the inner tubular member is coupled to the saddle member such that the inner tubular member moves axially with the saddle member while rotating relative to the saddle member.

A tissue removal system provided in accordance with some embodiments includes an outer tubular member having a closed distal end and a resection window proximal to the distal end; an inner tubular member disposed within the outer tubular member, the inner tubular member comprising a longitudinal axis and a distal end, wherein the distal end of the inner tubular member is movable across the resection window for cutting tissue extending through the resection window; a drive shaft coupled to the inner tubular member, wherein the drive shaft is configured to simultaneously rotate and oscillate axially; and a housing coupled to a proximal end of the outer tubular member, wherein a proximal end of the inner tubular member is disposed within, and configured to rotate and oscillate axially relative to, the housing, wherein a proximal end of the housing defines a lumen through which the drive shaft is received.

The tissue removal system may further include a reversible motor; a rotatable output shaft operatively coupled to the motor; and a connector for connecting the rotatable output shaft to the drive shaft in a manner that allows the drive shaft to rotate with, and oscillate axially relative to, the output shaft. In addition, the tissue removal system may include a disc fixedly coupled to the drive shaft, wherein the disc is tilted relative to a longitudinal axis of the drive shaft; and a fixed block comprising a groove configured for engaging an outer periphery of the disc, wherein rotation of the respective drive shaft and disc causes axial translation of the drive shaft due to the engagement between the disc and the fixed block.

A tissue removal system provided in accordance with some embodiments includes an outer tubular member having a closed distal end and a resection window proximal to the distal end; an inner tubular member disposed within the outer tubular member, the inner tubular member comprising a longitudinal axis and a distal end, wherein the distal end of the inner tubular member is movable across the resection window for cutting tissue extending through the resection window; a hollow rotational drive shaft coupled to the inner tubular member, and configured for rotating the inner tubular member about the longitudinal axis; a translational drive shaft disposed within the rotational drive shaft, and coupled to the inner tubular member for axially oscillating the inner tubular member; and a housing coupled to a proximal end of the outer tubular member, wherein a proximal end of the inner tubular member is disposed within, and configured to rotate and oscillate axially relative to, the housing, wherein a proximal end of the housing defines a lumen through which the rotational drive shaft and translational drive shaft disposed therein are received.

The tissue removal system may further include a rotational motor operatively coupled to the rotational drive shaft; and a translational motor operatively coupled to the translational drive shaft, wherein the rotational motor and the translational motor are independently operable.

A tissue removal system provided in accordance with some embodiments includes an outer tubular member having a closed distal end and a resection window proximal to the distal end; an inner tubular member disposed within the outer tubular member and configured to rotate and oscillate axially relative to the outer tubular member; a housing coupled to a proximal end of the outer tubular member, wherein a proximal end of the inner tubular member is disposed within, and configured to rotate and oscillate axially relative to, the housing; a reversible motor comprising a rotatable output shaft; a translational shaft coupled to the motor output shaft and to the inner tubular member, wherein the respective translational shaft and the output shaft are configured such that rotation of the output shaft in a first direction causes the inner tubular member to move axially in a first direction, and wherein rotation of the output shaft in a second direction opposite to the first direction causes the inner tubular member to move axially in a second direction opposite to the first direction; and a motor control switch disposed within the housing and operatively coupled to the motor, wherein actuating the switch reverses the motor output and causes the motor output shaft to change its direction of rotation, i.e., from rotation in the first direction to rotation in the second (opposite) direction, or from rotation in the second direction to rotation in the first direction. In one embodiment, the motor control switch is actuated when the inner tubular member is in a distal position relative to the housing, thereby ensuring that the tissue resection window is closed off prior to the inner tubular member changing its translational direction.

In one embodiment, the translational shaft includes a helical groove, wherein rotation of the output shaft causes rotation of the translational shaft. The helical groove may have a variable pitch, wherein windings in a first portion of the helical groove may be closer together than windings in a second portion of the helical groove. The tissue removal system may further include a carriage configured to engage the helical groove on the translational shaft, and to oscillate axially relative to the translational shaft when the translational shaft is rotating, wherein the carriage may be coupled to the inner tubular member such that the inner tubular member oscillates axially with, and rotates relative to, the carriage. In particular, the carriage may be configured to actuate the motor control switch (e.g., by mechanical contact) when the carriage is in a distal position relative to the housing, thereby ensuring that the tissue resection window is closed prior to actuation of the switch.

A tissue removal system provided in accordance with some embodiments includes an outer tubular member having a closed distal end and a resection window proximal to the distal end; an inner tubular member disposed within the outer tubular member, and configured to rotate and oscillate axially relative to the outer tubular member; a housing coupled to a proximal end of the outer tubular member, wherein a proximal end of the inner tubular member is disposed within, and configured to rotate and oscillate axially relative to, the housing; a translational shaft disposed within the housing, the translational shaft comprising a helical groove having a variable pitch, wherein windings in a first portion of the helical groove are closer together than windings in a second portion of the helical groove; and a carriage coupled to the inner tubular member and engaged with the helical groove, such that rotation of the translational shaft causes axial translation of the carriage and axial translation of the inner tubular member. The first portion of the helical groove may be positioned distally relative to the second portion of the helical groove.

The tissue removal system may further include a reversible motor comprising a rotatable output shaft operatively coupled to the translational shaft such that rotation of the output shaft in a first direction may cause the translation shaft to rotate in the first direction, and rotation of the output shaft in a second direction opposite to the first direction may cause the translational shaft to rotate in the second direction opposite to the first direction; and a motor control switch disposed within the housing and operatively coupled to the motor, wherein actuation of the switch reverses the motor output and causes the motor output shaft to change from rotating in the first direction to rotating in the second direction, or from rotating in the second direction to rotating in the first direction.

Additional aspects, features and advantages of the disclosed inventions are set forth in part in the description which follows, and will also in part be apparent from the description or may be learned by practice of the invention. In the description, reference is made to the accompanying drawings which form a part thereof and in which is shown by way of illustration various embodiments for practicing the inventions. Although the embodiments are described in sufficient detail to enable those skilled in the art to practice the disclosed inventions, it is to be understood that other embodiments may be utilized and that structural changes may be made without departing from the scope of the inventions, which are defined by the claims appended hereto. The following detailed description is, therefore, for purposes of illustration, and is not to be taken in a limiting sense.

BRIEF DESCRIPTION OF THE DRAWINGS

The foregoing and other features, aspects and advantages of the embodiments of the inventions disclosed herein are described in detail below with reference to the drawings of various embodiments, which are intended to illustrate and not to limit the inventions. The drawings comprise the following figures in which.

DETAILED DESCRIPTION OF THE ILLUSTRATED EMBODIMENTS

Although several embodiments, examples and illustrations are disclosed below, it will be understood by those of ordinary skill in the art that the inventions described herein extend beyond the specifically disclosed embodiments, examples and illustrations, and may include other uses of the disclosed inventions and obvious modifications and equivalents thereof. Embodiments are described with reference to the accompanying figures, wherein like numerals refer to like elements throughout. The terminology used in the description presented herein is not intended to be interpreted in any limited or restrictive manner simply because it is being used in conjunction with a detailed description of some specific embodiments. In addition, the illustrated and described embodiments may comprise several novel features and no single feature is solely responsible for its desirable attributes or is essential to practicing the inventions herein described.

The various embodiments provide novel methods, systems and devices for tissue access, diagnosis, and/or removal. The methods, systems and devices are disclosed in the context of hysteroscopes and methods utilizing hysteroscopes because they have particular utility in this context. The embodiments disclosed herein, however, may also be used in other contexts, such as, for example, but without limitation, surgical tools with components that both rotate and translate.

Figure 1:
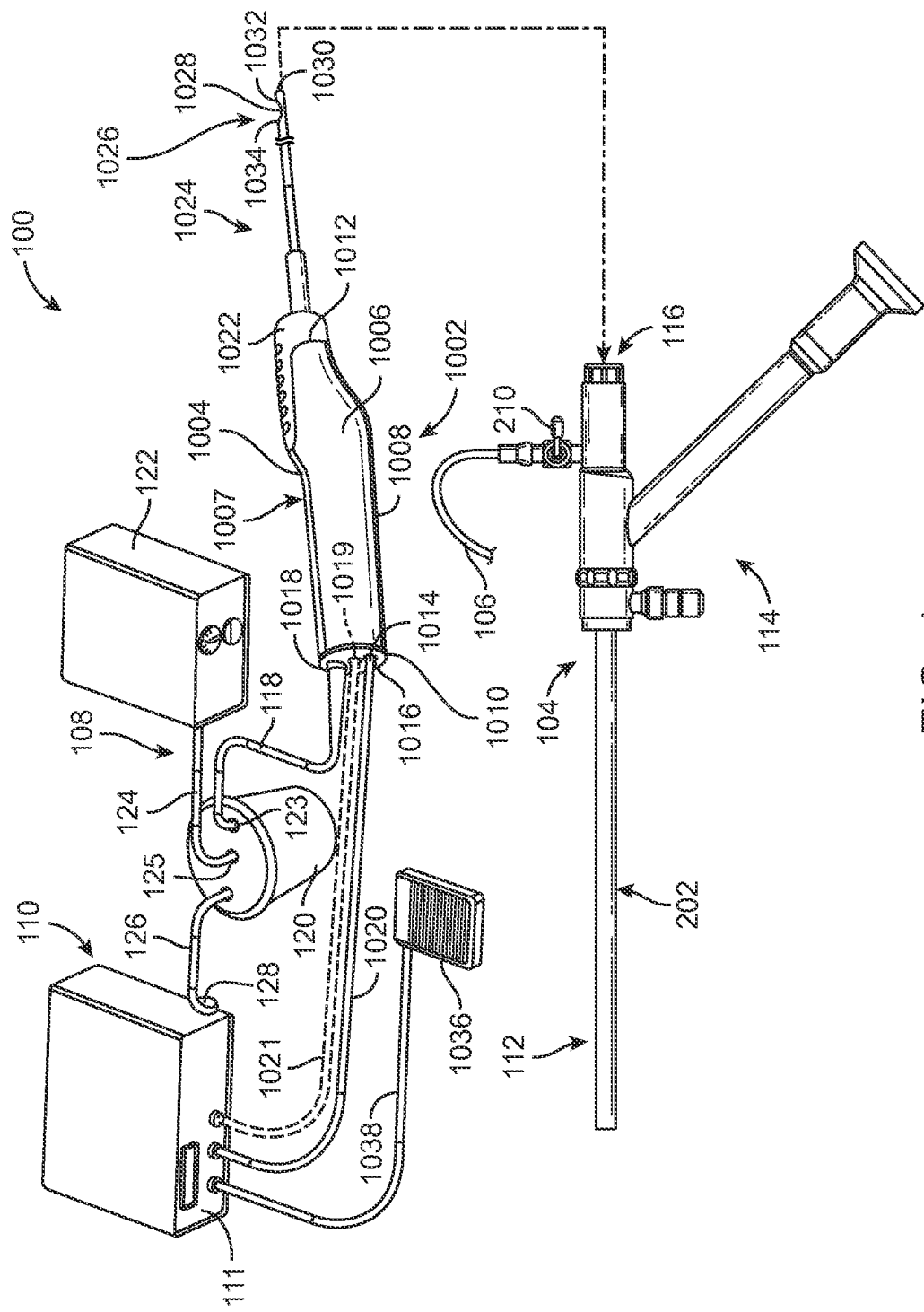
FIG. 1 is a partially exploded perspective view of an embodiment of a morcellator system.

FIG. 1 schematically illustrates a surgical access and tissue removal system 100. In this case, an access device and morcellator have been selected to illustrate the principles of the embodiments. However, it will be understood that such principles apply equally to all types of surgical access devices, as well as to devices not necessarily limited to surgical access. Generally, the embodiments disclosed herein include devices, such as a working channel or other types of lumens, where it is desirable to provide simultaneous inflow and outflow of fluid while receiving various surgical instruments through the working channel or lumen. Such devices may include, without limitation, hysteroscopes, endoscopes, catheters, cannulas, and the like. Thus, the embodiments described with respect to a morcellator intended for gynecological procedures are illustrative only, and not intended to be limiting in any respect.

With further reference to FIG. 1, the surgical access and tissue removal system 100 may be considered a surgical access system 100 configured for gynecological procedures, such as hysteroscopy, cystoscopy, and arthroscopy. However, a wide variety of procedures may be performed with the system 100. In addition to the performance of one or more gynecological procedures described in detail herein, the systems, methods, apparatuses, and devices disclosed herein may be used to perform one or more additional procedures (for example, urological procedures or the like), including, but not limited to, access and tissue manipulation and/or tissue removal from any of a variety of organs and tissues, such as the bladder, breast, lung, stomach, bowel, esophagus, oral cavity, rectum, nasal sinus, Eustachian tubes, heart, gall bladder, spine, shoulder, knee, hip, brain, arteries, veins, and various ducts. Routes of access include but are not limited to trans-cervical; trans-vaginal-wall; trans-uteral; trans-vesicle; trans-urethral; and other routes.

The surgical access and tissue removal system 100 illustrated in FIG. 1 includes a tissue removal device 1002, an access device 104, a fluid supply 106, a vacuum assembly 108, and a motor drive assembly unit 110. The access device 104 includes a distal insertion portion 112, which is intended for insertion into the patient's body, and a proximal portion 114, which generally remains outside the patient's body. In this embodiment, the access device 104 is a hysteroscope, wherein access to the patient's body is achieved through the cervix. However, the access device 104 may alternatively be any of a wide variety of other instruments, such as endoscopes, catheters, cannulas, and the like, and access may be gained through other natural openings or orifices in the body, for example, ears, nose, mouth, via trans-rectal, urethral, vaginal, or through surgical incision, or the like.

The distal portion 112 of the access device 104 includes a straight rigid rod and/or shaft 202 for insertion into the patient's vaginal opening and through the cervix to access the uterine cavity. However, in some embodiments, the distal portion 112 is flexible and/or semi-flexible. In some embodiments, the rigid rod and/or shaft 202 comprises an optical system and/or visualization element and a working channel. A wide variety of surgical instruments may be inserted into the working channel of the shaft 202. For example, the working channel may be configured to receive a removable outflow channel or the tissue removal device 1002. In some embodiments, the working channel may have an area of 14.1 mm sq.

The rod or shaft 202 of the access device of 104 may be dimensioned to enter a wide variety of natural body orifices and/or surgical sites and/or incisions. In the case of gynecological procedures wherein the rigid shaft 202 enters the cervix, the shaft 202 may have a diameter of 6.25 mm to minimize pain, discomfort, and/or injury to the patient while maximizing the cross-sectional area of the shaft 202. A 6.25 mm diameter size will generally require local anesthesia because substantial dilation of the cervix may be required. However, the access device 104 may be configured with shafts 202 having other diameter sizes, for example, 2 mm, 3 mm, 4 mm, 5 mm, 6 mm, 7 mm, 8 mm, 9 mm, 10 mm, 11 mm, and 12 mm, and preferably between 5 mm-8 mm to minimize patient discomfort and/or injury while maximizing the cross-sectional area of the shaft 202.

In some embodiments, the cross-sectional shape of the shaft 202 is substantially oval and/or elliptical to provide the working channel a greater cross-sectional area and/or to allow the shaft 202 to pass more easily through the body orifice and/or the surgical site/incision.

The proximal portion 114 of the access device 104 includes an instrument input opening 116. A medical instrument, such as the tissue removal device 1002, may be inserted into the opening 116, and through the working channel that extends through the shaft 202.

A surgeon using the hysteroscope 104 for a surgical procedure may open, close, and/or limit the amount of fluid flowing into an fluid inflow conduit and into the patient's body, here the uterine cavity, by adjusting the inflow fluid stopcock 210. With the tissue removal device 1002 inserted into the working channel of the hysteroscope 104, fluid from the fluid supply 106 may enter the body by flowing through inflow fluid stopcock 210 and into the working channel and around the tissue removal device 1002. An area within the tissue removal device 1002 acts as a fluid outflow conduit, which is in fluid communication with an evacuation tube 118. The evacuation tube 118, in turn, is in fluid communication with the vacuum assembly 108.

The tissue removal device 1002 is configured for removing tissue from the body, in this case fibroids and other abnormal tissue from the uterine cavity. In some embodiments, the tissue removal device 1002 has a cutting mechanism, which includes an outer tubular member 1024 and an inner tubular member 1028. Inner tubular member 1028 moves rotationally and, at the same time, oscillates translationally relative to outer tubular member 1024 in a manner to be described further below. The outer tubular member 1024 is configured for insertion into the working channel of the shaft 202.

The tissue removal device 1002 may be of the type described in U.S. patent application Ser. No. 12/432,647, titled "ACCESS DEVICE WITH ENHANCED WORKING CHANNEL," which is hereby incorporated by reference in its entity. The tissue removal device 1002 may comprise complementary left and right housing halves 1004 and 1006, respectively, each of which may be made of a rigid polymer or other suitable material. Halves 1004 and 1006 may be joined together, for example, with screws to form an elongated hollow housing 1007 comprising a rounded side wall 1008, an open proximal end 1010, and an open distal end 1012. Housing 1007 may be bent or otherwise ergonomically shaped to fit comfortably in the hand of a user.

A proximal cap 1014 may be mounted in the proximal end 1010 of the housing 1007. The proximal cap 1014 may include a pair of openings or lumens 1016 and 1018. Opening or lumen 1016 may be configured to receive a flexible drive cable within protective sheath 1020, which is mechanically coupled to one or more motors within the motor drive assembly unit 110. Opening or lumen 1018 may be configured to receive the evacuation tube 118. The proximal cap 1014 may further comprise a third opening 1019. The optional third opening 1019 may be configured to receive, for example, an additional flexible drive cable with a protective sheath 1021, which is mechanically coupled to another motor within the motor drive assembly unit 110, described in greater detail below. Embodiments having a single flexible drive cable, as well as embodiments having two flexible drive cables, are discussed in greater detail below.

A distal cap 1022 may be mounted in the distal end 1012 of the housing 1007. The distal cap 1022 may include an opening or lumen, which may receive the outer tubular member 1024.

The outer tubular member 1024 may have an outer diameter of about 3.0 mm for insertion into the working channel of the shaft 202 of the access device 104. However, in some embodiments, the outer diameter of the tubular member 1024 may be 5.5 mm or less, or more preferably 4 mm or less, even more preferably 3 mm or less, and still even more preferably 2 mm or less. In some embodiments, the tubular member 1024 may have a circular cross-sectional shape. However, other cross-sectional shapes, such as oval or elliptical, are possible to maximize fluid flow and/or tissue cutting and/or removal. With a smaller outer diameter, the tissue removal device 1002 may cause less patient discomfort, reduce the risk of injury to the patient, and/or obviate or reduce the need for anesthesia to be administered to the patient. However, if the tissue removal device 1002 is used in an operating room setting where general anesthesia is available, and/or if the working channel is configured to receive a tissue removal device with a larger diameter, the tubular member 1024 diameter may be increased to maximize tissue removal and/or fluid flow. In such a case, the tubular member 1024 may have a diameter generally less than about 12 mm, preferably less than about 11 mm, and, for some applications, less than 10 mm. Depending on the particular clinical application, the tubular member 1024 may be constructed to have an outer diameter of no more than about 9 mm, in some applications less than about 8 mm, preferably less than 7 mm, and more preferably less than 6 mm where the outer diameter is desirably minimized.

Outer tubular member 1024, which may be a unitary structure made of stainless steel or another similarly suitable material, may be shaped to include an open proximal end, a closed distal end 1030, and a lumen extending from the open proximal end to a point just prior to closed distal end 1030. The proximal end of the outer tubular member 1024 may be fixed to the distal end of the housing 1007.

Outer tubular member 1024 may be further shaped to include a resection window 1026. When vacuum is applied to the outer tubular member 1024, the resection window 1026 may receive, capture, and/or draw in tissue, fluid, and/or other matter. The window 1026 may be located proximate to the distal end 1030, such as, for example, 0.25 inch from the distal end 1030. The window 1026 may be shaped to include a proximal end 1034 and a distal end 1032. The proximal end 1034 may slope gradually proximally, and the distal end 1032 may slope gradually distally. The proximal end 1034 of the resection window 1026 may be a radial end having a radius of curvature of, for example, 0.085 inches; however, other radius curvatures are possible. The distal end 1032 of resection window 1026 may be a radial end having a radius of curvature of, for example, 0.150 inches; however, other radius curvatures are possible. The slopes of the proximal and distal ends 1032, 1034 may allow or encourage tissue to enter the resection window 1026. In some embodiments, the slopes of the proximal and distal ends 1032, 1034 form cutting edges for tissue resection. The resection window 1026 may have a length of approximately 0.55 inches. However, other lengths are possible. The resection window 1026 may extend over a substantial portion of the circumference of the outer tubular member 1024, such as, for example, about 60% of the circumference; however, other percentages are possible.

The inner tubular member 1028 may include a proximal end, a distal end, and a longitudinal lumen. The distal end of the inner tubular member 1028 may be shaped to include an external bevel, such as, for example, an external bevel of approximately 20 degrees. Tubular members 1024 and 1028 may be arranged so that, when tubular member 1028 is in a fully retracted, proximal-most position, distal end of tubular member 1028 may be withdrawn sufficiently to permit tissue to enter window 1026 (preferably with distal end of tubular member 1028 positioned proximal to window 1026), and so that, when tubular member 1028 is in a fully advanced, distal-most position, distal end of tubular member 1028 may be positioned distally of distal end 1032 of window 1026. In this manner, as tubular member 1028 is moved translationally and rotationally past window 1026, tissue within window 1026 may be sheared. To promote such a shearing of tissue, the outer diameter of inner tubular member 1028 may be just slightly less (e.g., about 0.002 inch) than the inner diameter of outer tubular member 1024.

The vacuum assembly 108 may comprise a specimen collection/fluid container 120 and a vacuum source 122. The distal end of the evacuation tube 118 may be connected to the proximal end of the outer tubular member 1024 through lumen 1018, and the proximal end of the evacuation tube 118 may be coupled to a first port 123 of the container 120. A distal end of a tube 124 may be coupled to a second port 125 of container 120, and the proximal end of tube 124 may be coupled to the vacuum source 122. In this manner, the vacuum source 122 may be used to apply suction to the tissue removal device 1002, and any withdrawn tissue, fluids, or other matter suctioned through the resection window 1026 of the tissue removal device 1002 may be collected in container 120.

Motors connected to proximal ends of the external drive shafts within the protective sheaths 1020 and 1021 may be coupled to a source of electricity, such as an AC wall outlet, using a power cord (not shown), and/or may be included within the motor drive assembly unit 110, in which there may be disposed other electronics (not shown). Distal ends of the external drive shafts within the protective sheaths 1020 and 1021 pass through the lumens 1016 and 1019 in the proximal cap 1014 of the housing 1007, and are coupled to the inner tubular member 1028. One or more motor control switches may be employed for turning on/off the respective one or more motors disposed within the unit 110. Such a motor control switches may be actuated by a user. As an example of such a motor control switch, a foot pedal 1036 may be coupled to the motors by a cable 1038, and the foot pedal 1036 may be used as a power switch to selectively activate or de-activate the motors.

The motor drive assembly unit 110 may include a vacuum sensor 128, which may be coupled to the container 120 by a tube 126, so that the pressure within the container 120 may be monitored. In this manner, a sudden increase in vacuum pressure may indicate that a clog has occurred. The presence of a clog may be indicated via an alarm (not shown) located on or within the motor drive assembly unit 110. The detection of a clog may indicate that further operation of the tissue removal device 1002 would only aggravate the clogging situation and that a cessation of tissue removal may be necessary. In this case, the motor drive assembly unit 110 may be configured to turn off and/or deactivate the vacuum source 122 and/or the motor. Similarly, a decrease in vacuum pressure, sudden or otherwise, may indicate that the tissue removal device 1002 has been removed from the working channel of the access device 104. With the tissue removal device 1002 removed, the inflow fluid cannot be removed from the body. In this case, the motor drive assembly unit 110 may be configured to turn off and/or deactivate the vacuum source 122.

The motor drive assembly unit 110 may be configured to synchronize actuation of the motor with actuation of the vacuum source 122. In this manner, turning on the motor will turn on the vacuum source 122 at the same time. Correspondingly, the vacuum source 122 may be deactivated whenever the motor is turned off or when the tissue removal device 1002 is removed from the access device 104.

Figure 2:
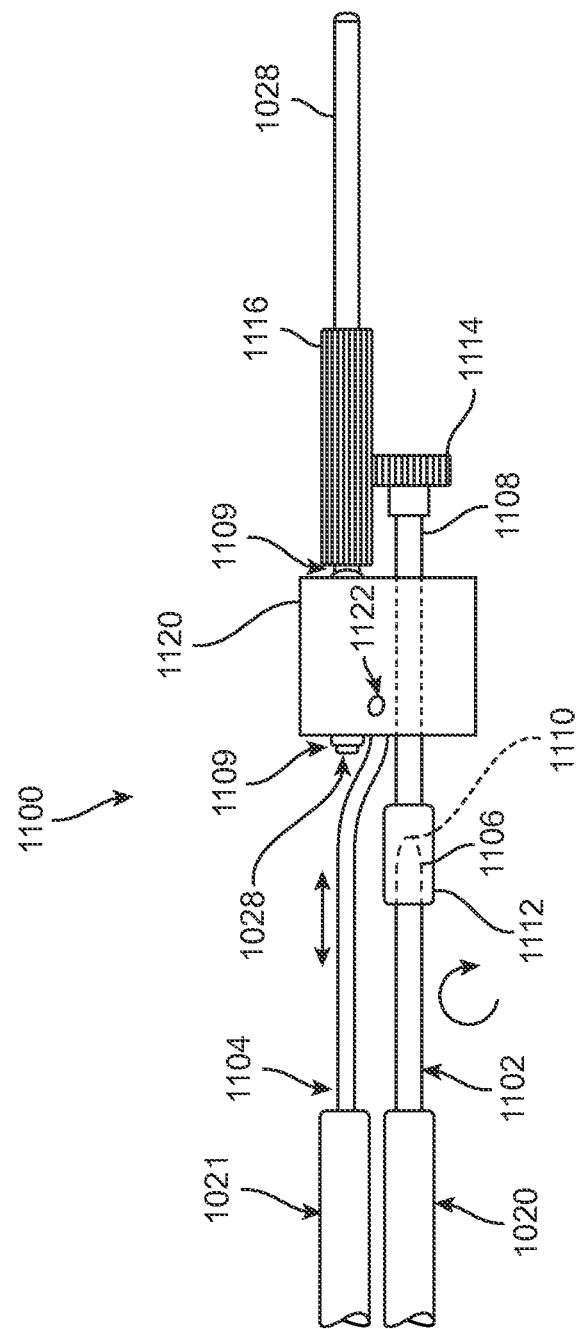
FIG. 2 is a schematic diagram illustrating the connections of two cables, one rotational cable and one push/pull cable for rotating and translating the cutter of the morcellator illustrated in FIG. 1.

One embodiment of a drive system 1100 for transferring rotational and translational movements from external drive shafts to the inner tubular member 1028 is schematically illustrated in FIG. 2. This drive system 1100 includes two drive shafts 1102 and 1104, mounted within the sheaths 1020, 1021, respectively, for both rotating and translating the inner tubular member 1028. For simplicity, the housing 1007 is omitted to reveal the inner components connecting the shafts 1102 and 1104 to the inner tubular member 1028. Although not shown in FIG. 2, it should be well understood that, in this embodiment, the proximal cap 1014 of the housing 1007 includes lumen 1016 as well as lumen 1019, so that the housing 1007 is configured for receiving two flexible drive cables.

As illustrated in FIG. 2, shaft 1102 is a rotational shaft, which may be in the form of any type of flexible transmitter commonly used for rotating tools. In the illustrated embodiment, the rotational shaft 1102 includes a connection 1106 between the rotational shaft 1102 and a distal portion 1108. The connection 1106 may include a collar 1112 connected to the distal portion 1108 and receiving a distal tip 1110 of the rotational shaft 1102. Such a connection 1106 may include splines, a key way, adhesive, or any other type of device which can transmit rotational energy. As such, rotational energy from the rotational shaft 1102 may be transmitted to the distal tip 1110 and thus to the collar 1112 to thereby rotate the distal portion 1108.

The distal portion 1108 may include a rotational drive gear 1114 rotationally mated to the distal portion 1108. Additionally, the distal portion 1108 may be rotationally supported by the housing 1007 with bearings (not shown). Thus, as the distal portion 1108 is rotated along with the rotational shaft 1102, the rotational gear 1114 also rotates.

In order to receive rotational energy from, and thereby rotate along with, the distal portion 1108, the inner tubular member 1028 may include a driven gear (e.g., pinion gear) 1116. The teeth of the driven gear 1116 may be configured to mate with and engage with the teeth on the drive gear 1114. Thus, as the distal portion 1108 rotates, thereby rotating the drive gear 1114, the driven gear 1116 also rotates. The driven gear 1116 is rotationally mated with the inner tubular member 1028, thereby rotating therewith. The driven gear 1116 is elongated, allowing the driven gear 1116 to move axially relative to the gear 1114 while remaining meshed with the gear 1114.

As illustrated in FIG. 2, shaft 1104 is a translational shaft. Translational shaft 1104 may be a push/pull type of cable, which may be configured to be a stiff member that may be loaded both in tension and compression for moving components of a mechanism. In the illustrated example, the translational shaft 1104 is connected to a saddle member 1120 at a connection 1122. The saddle 1120 may be engaged to the inner tubular member 1028 such that the inner tubular member 1028 may rotate relative to the saddle member 1120, but is engaged such that the saddle member 1120 and the inner tubular member 1028 move axially together.

For example, the inner tubular member 1028 may include circumferential grooves mating with one or more snap rings 1109 or other engaging device, mounted to or engaging the saddle member 1120 such that the saddle member 1120 and the inner tubular member 1028 remain coupled together while allowing the inner tubular member 1028 to rotate relative to the saddle member 1120. Thus, as the translational shaft 1104 is moved distally and proximally, the saddle member 1120 is also moved distally and proximally, thereby moving the inner tubular member 1028 axially, in a reciprocal manner, relative to the outer tubular member 1024.

Figure 3:
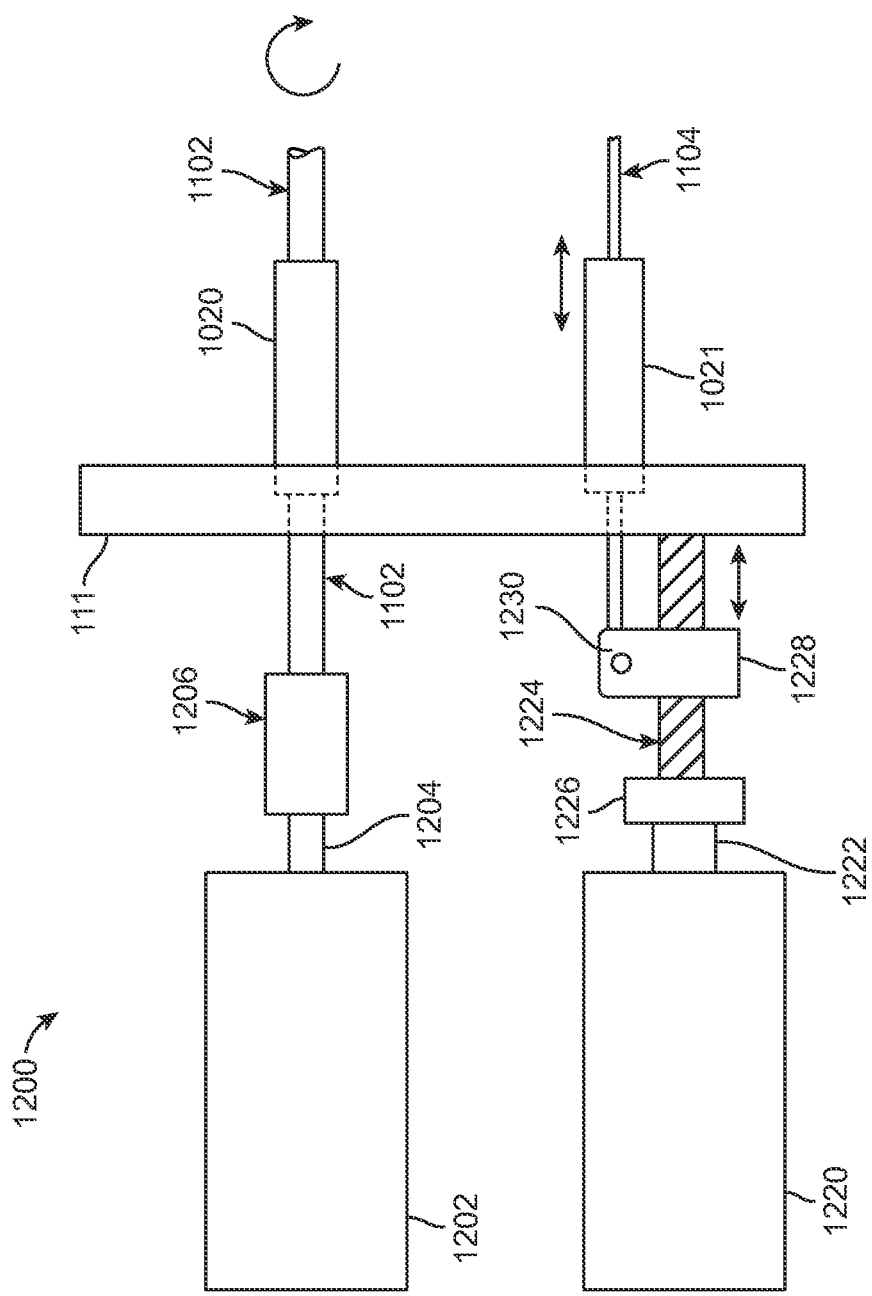
FIG. 3 is a schematic diagram illustrating a motor arrangement used to drive the two cables illustrated in FIG. 2.

One embodiment of a motor arrangement 1200 is illustrated in FIG. 3. The motor arrangement 1200 is an example of an arrangement of motors that may be used to drive the shafts 1102 and 1104 of the drive system 1100 illustrated in FIG. 2. However, other arrangements may also be used.

The motor arrangement 1200 includes a rotational motor 1202 and a translational motor 1220. The motors 1202, 1220 may be operated independently to output the desired rotational rate and translational rate of reciprocation.

In the illustrated embodiment, the rotational shaft 1102 is driven by the rotational motor 1202. The rotational motor 1202 may have an output shaft 1204 connected to the rotational shaft 1102 with a shaft coupling mechanism 1206. The rotational shaft 1102 extends through a front face 111 of the unit 110 (FIG. 1). The motor 1202 and shafts 1204, 1102 may be supported by the unit 110 and/or the front face 111 with any arrangement of bearings or other support devices.

In this arrangement, the rotational motor 1202 rotates its output shaft 1204 in response to an input signal, such as a power signal from other devices within the unit 110. As such, the rotational speed of the shaft 1204 can be controlled as desired.

The translational motor 1220 may be coupled to the translational shaft 1104. In the illustrated embodiment, the translational drive motor 1220 is an electric motor with a rotating output shaft 1222. The rotational output shaft 1222 is connected to a worm gear 1224 with a shaft coupling mechanism 1226. A follower mechanism 1228 may include internal teeth configured to follow the helical groove on the exterior surface of the worm gear 1224, to thereby translate as the worm gear 1224 is rotated. Thus, as the output worm gear 1224 is rotated clockwise, the follower 1228 may translate proximally toward the motor 1220 and as the worm gear 1224 is rotated counter-clockwise, the follower 1228 may move distally away from the motor 1220.

The translational shaft 1104 may be connected to the follower 1228 at a connection point 1230. Thus, as the follower 1228 translates distally and proximally, the push/pull cable 1104 also moves distally and proximally.

Similar to the rotational motor 1202, the translational motor 1220 may be driven by the unit 110 to rotate clockwise and counter-clockwise at a speed to provide the desired rate of reciprocation. The arrangement 1200 may include a motor control switch where activation of the switch sends a signal to the translational motor 1220 to reverse the motor 1220 and cause the rotating output shaft 1222 of the motor 1220 to change from clockwise rotation to couter-clockwise rotation, or vice versa. The motor control switch is discussed in more detail below with reference to FIGS. 9(*a*) and 9(*b*).

Figure 4:
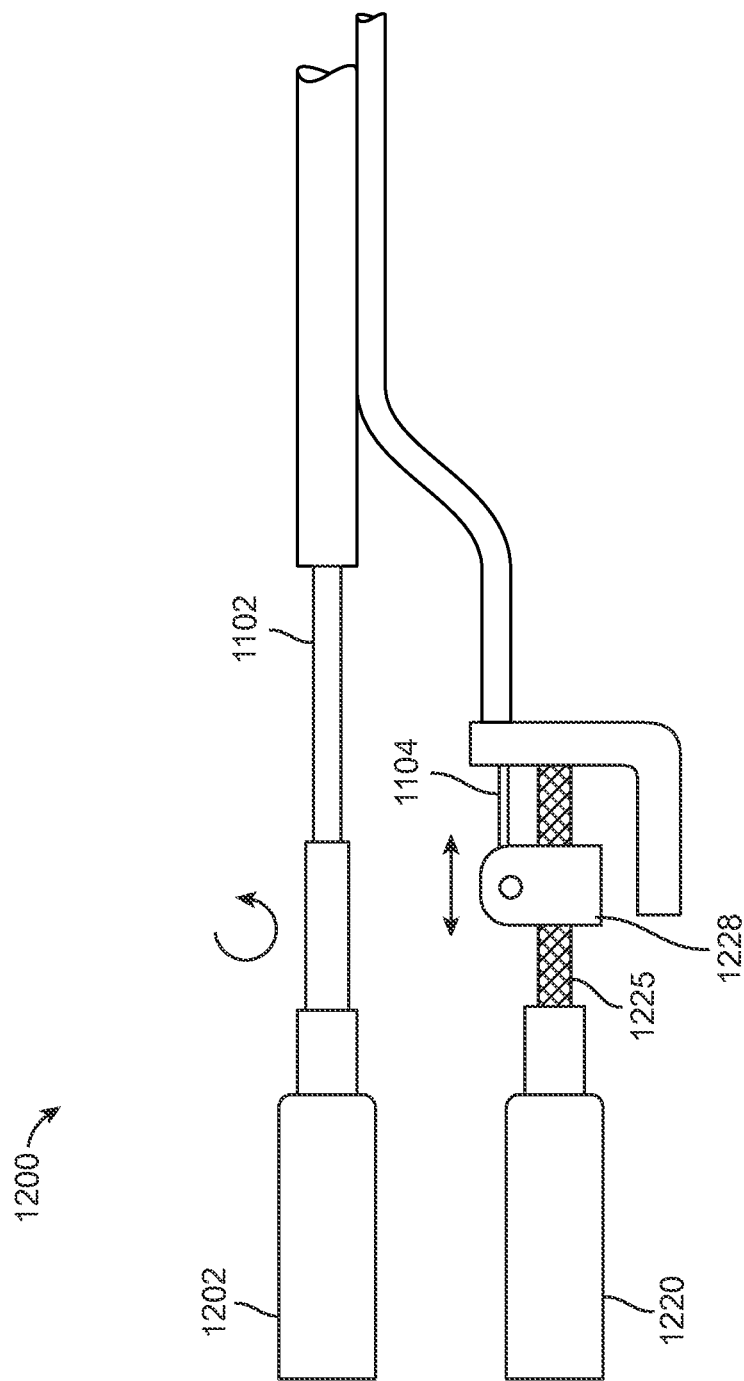
FIG. 4 is a further embodiment of the motor arrangement illustrated in FIG. 3.

The worm gear 1224 in FIG. 3 has a single helix groove. Thus, when the follower mechanism 1228 reaches the proximal end or the distal end of the worm gear 1224, the output shaft 1222 of the motor 1220 changes direction so that the worm gear 1224 rotates in the opposite direction, thus causing the follower mechanism 1228 to move axially towards the other end of the gear 1224. However, in other embodiments, the worm gear may include a double helix groove. For example, as shown in FIG. 4, the drive arrangement 1200 may include a double helix worm gear 1225 having a right-hand threaded helical groove and a left-hand threaded helical groove. The two helical grooves may be blended together at their respective ends to form a continuous groove so that there may be a smooth transition from one helical groove to the other. Thus, the drive motor 1220 may be rotated in a single direction yet achieve a reciprocating translational movement of the follower 1228, both proximally and distally in a cyclical manner during a constant rate of rotation of the worm gear 1225.

In other embodiments, the motor 1220 may be a simple linear actuator with a more direct connection to the push/pull cable 1104, and, with appropriate driver electronics, may directly drive the push/pull cable 1104 distally and proximally along a translation direction.

Figure 5:
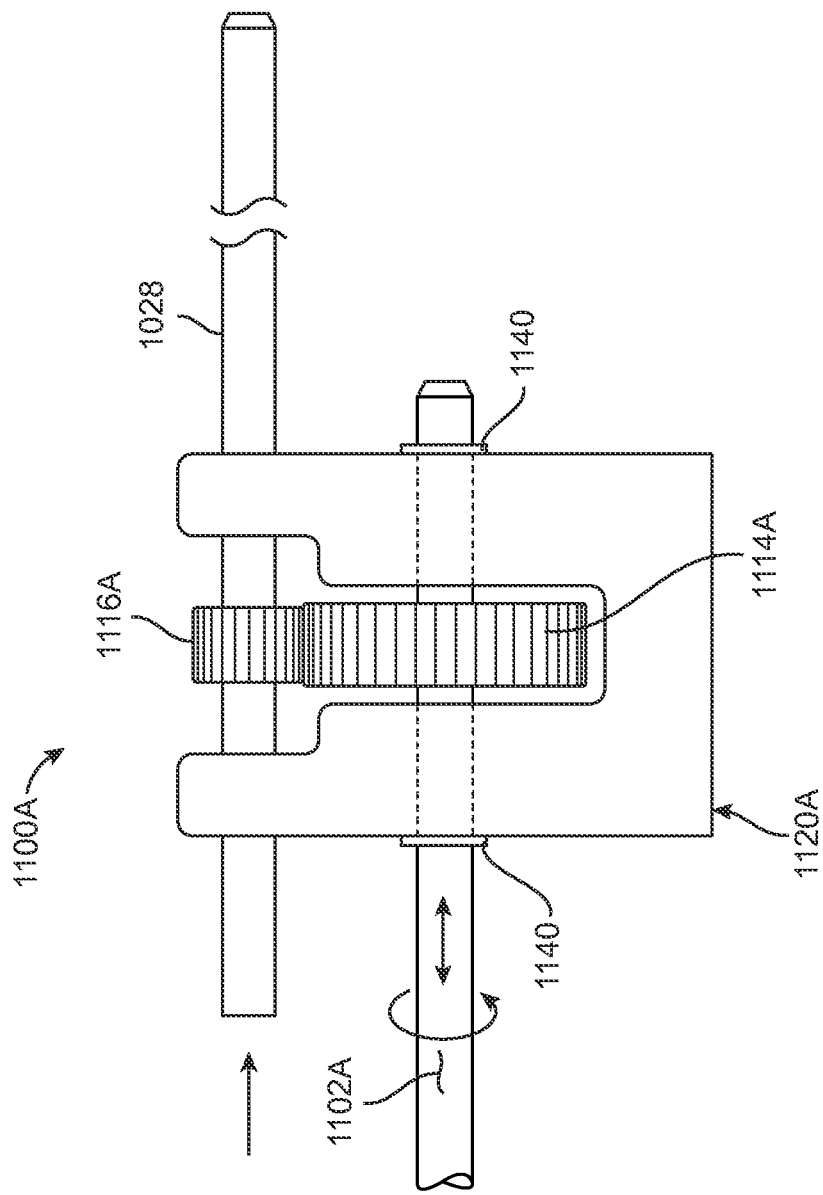
FIG. 5 is an embodiment of the drive illustrated in FIG. 2 including a single cable that is both rotated and translated so as to drive the cutter blade rotationally and translationally.

With reference to FIG. 5, a further embodiment of a drive system for transferring rotational and translational movements from an external drive shaft to the inner tubular member 1028 is illustrated and identified with the reference numeral 1100A. Components of the drive system 1100A that are similar to those of the drive system 1100 illustrated in FIG. 2 are identified with the same reference numeral, except that the letter "A" has been added thereto.

The drive system 1100A may receive both rotational and translational energy from a single shaft 1102A which is driven both rotationally and translationally, as described in greater detail below. The shaft 1102A, as described above with reference to FIG. 2, may extend into the housing 1007 for both reciprocal and translational movement. In this embodiment, the optional third opening 1019 in the proximal cap 1014 of the housing 1007 is not needed.

The drive gear 1114A is rotationally attached to the drive shaft 1102A so as to rotate therewith and is meshed with the driven gear 1116A. The driven gear 1116A is rotationally attached to the inner tubular member 1028. Additionally, the saddle 1120A is connected to the shaft 1102A so as to translate therewith. For example, in the illustrated embodiment, the drive 1100A may include snap rings 1140 engaged with circumferential grooves (not shown) on the exterior surface of the shaft 1102A to thereby cause the saddle member 1120A to move translationally with the shaft 1102A while allowing the shaft 1102A to rotate relative to the saddle member 1120A. A similar arrangement (not shown) may be used to connect the saddle member 1120A with the inner tubular member 1028. Thus, as the shaft 1102A is rotated, the drive gear 1114A drives the driven gear 1116A, and thereby rotates the inner tubular member 1028. Similarly, as the shaft 1102A is translated proximally and distally, the saddle member 1120A is also translated proximally and distally, and therefore, so is the inner tubular member 1028.

Figure 6:
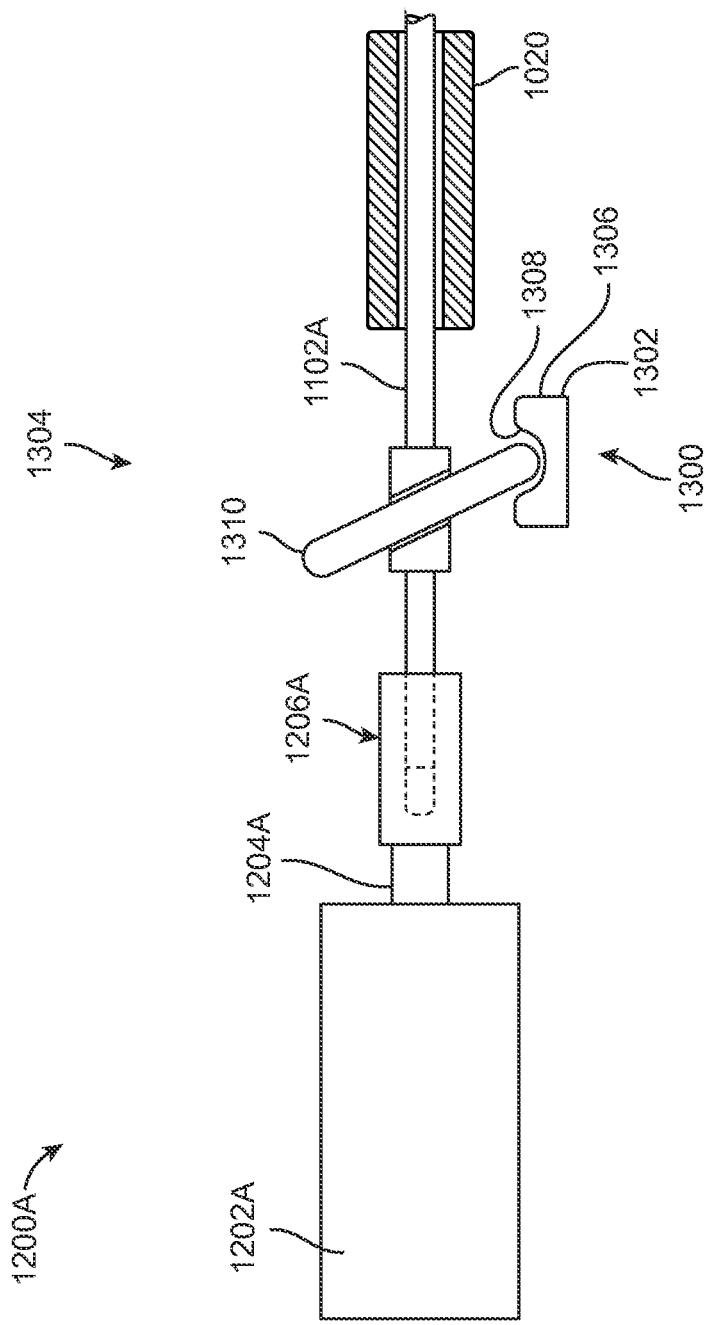
FIG. 6 is a schematic diagram of an embodiment of a drive mechanism for driving the cable illustrated in FIG. 5 so as to rotate and translate.

With reference to FIG. 6, a further embodiment of a motor arrangement is illustrated therein and identified with the reference numeral 1200A. Components of the motor arrangement 1200A that are similar to the motor arrangements 1200 depicted in FIGS. 3 and 4 are identified with the same reference numerals, except that an "A" has been added thereto.

As noted above with reference to FIG. 5, the drive 1100A may include a drive shaft 1102A that is both rotated and translated. The motor arrangement 1200A is an example of a motor arrangement that can both rotate and translate a shaft, such as the shaft 1102A.

As shown in FIG. 6, the motor arrangement 1200A includes a rotational motor 1202A which includes an output shaft 1204A that rotates as the motor 1202A is operated. The output shaft 1204A may be connected to the shaft 1102A in any known manner that allows for both the rotation and translation.

For example, the motor arrangement 1200A may include a connector 1206A for transmitting rotational energy from the output shaft 1204A to the shaft 1102A. In some embodiments, the connector 1206A may be configured to provide a splined connection between itself and the shaft 1102A. For example, the connector 1206A may include internal splines mating with splines on an external surface of the shaft 1102A which thereby provide for the transmission of rotational energy, yet allow for relative axial movement of the shaft 1102A relative to the connector 1206A.

The motor arrangement 1200A may also include a translational mechanism 1300 which is configured to cause a translational movement, proximally and distally, of the shaft 1102A. For example, in the illustrated embodiment, the mechanism 1300 includes a fixed block 1302 and a rotational member, such as a tilted, rotating disk 1304, configured to mate with the block 1302. In the illustrated embodiment, the fixed block 1302 includes a body 1306 fixed to the housing of the unit 110 (FIG. 1) and a groove 1308 configured to receive a portion, such as the outer periphery 1310, of the tilted disk 1304. The tilted disk 1304 may be rotationally connected to rotate with the shaft 1102A. Thus, as the tilted disk 1304 is rotated, the outer periphery 1310 of the tilted disk 1304 rides in the groove 1308, thereby driving the shaft 1102A both distally and proximally in a reciprocating fashion as the shaft 1102A is rotated. The translational mechanism 1300 illustrated in FIG. 6 is only one embodiment that may be used in the arrangement 1200A. Other mechanisms may also be used.

Figure 7:
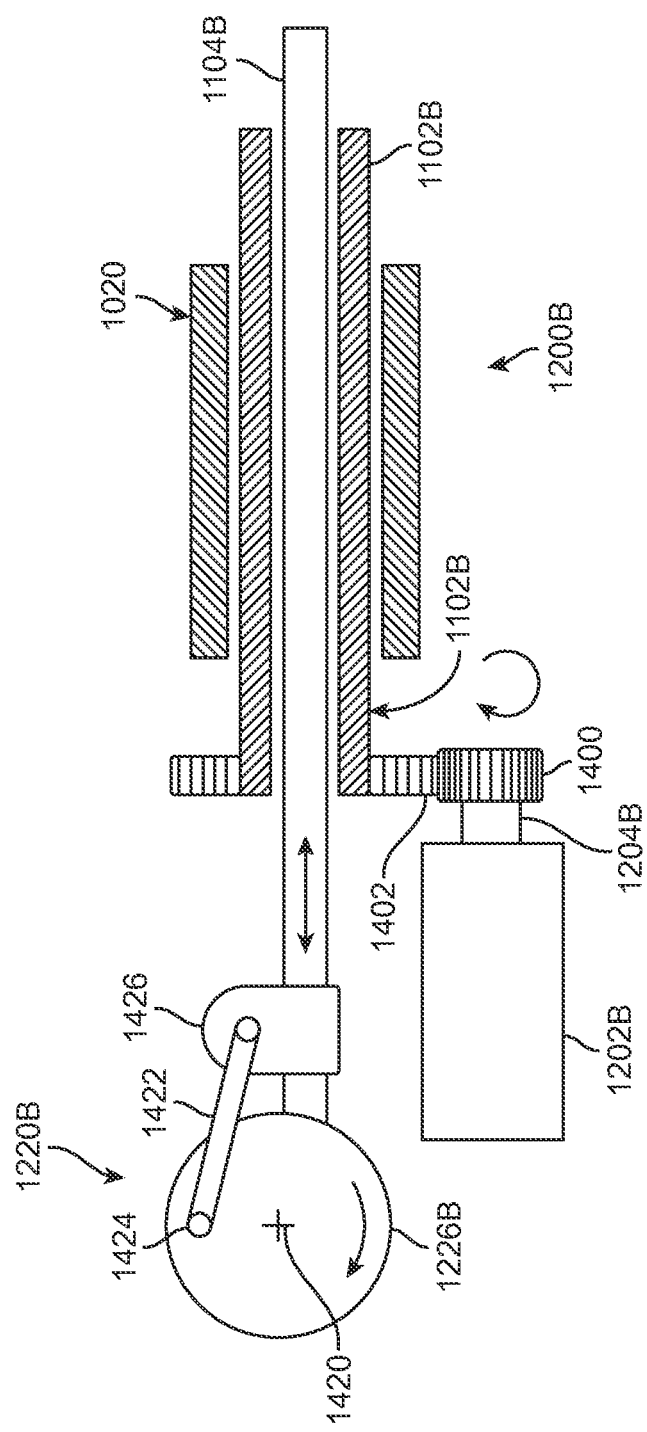
FIG. 7 is another embodiment of a drive using a push/pull cable extending through a hollow center of a rotational drive cable for both rotating and translating the cutter member of the morcellator.

With reference to FIG. 7, a further embodiment of a motor arrangement is illustrated therein and identified by the reference numeral 1200B. Components of the motor arrangement 1200B that are similar to the motor arrangements 1200 and 1200A illustrated in FIGS. 3, 4, and 6 are identified with the same reference numeral, except that a letter B has been added thereto.

With reference to FIG. 7, the motor arrangement 1200B may be configured to provide for a translational driving of the shaft 1104B and the rotational drive of the shaft 1102B, wherein the translational shaft 1104B moves reciprocally, proximally and distally, within the (hollow) rotational shaft 1102B. The motor arrangement 1200B includes a rotational motor 1202B having an output shaft 1204B connected to a drive gear 1400. As such, the motor 1202B may be driven to rotate the drive gear 1400. A driven gear 1402 is meshed with the drive gear 1400 and rotationally connected to the rotational shaft 1102B, such that as the drive gear 1400 is rotated, so is the rotational shaft 1102B.

The motor arrangement 1200B also includes a translational drive motor 1220B which has an output shaft (not shown) connected to a drive gear 1226B. The drive gear 1226B rotates about the axis 1420, which may be the rotational axis of the output shaft of the motor 1220B. A link member 1422 may be connected at one end 1424 to the drive gear 1226B at a position offset from the rotational axis 1420. The opposite end of the link member 1422 may be connected to a follower 1426. The follower 1426 may be connected to the translational shaft 1104B so as to translate therewith. Thus, as the drive gear 1226B is rotated, one end 1424 of the link member 1422 is rotated therewith, thereby driving the follower 1426 in a translational movement, reciprocating proximally and distally as the drive gear 1226B rotates. Thus, when the translational motor 1220B is driven, the translational shaft 1104B translates therewith.

Figure 8:
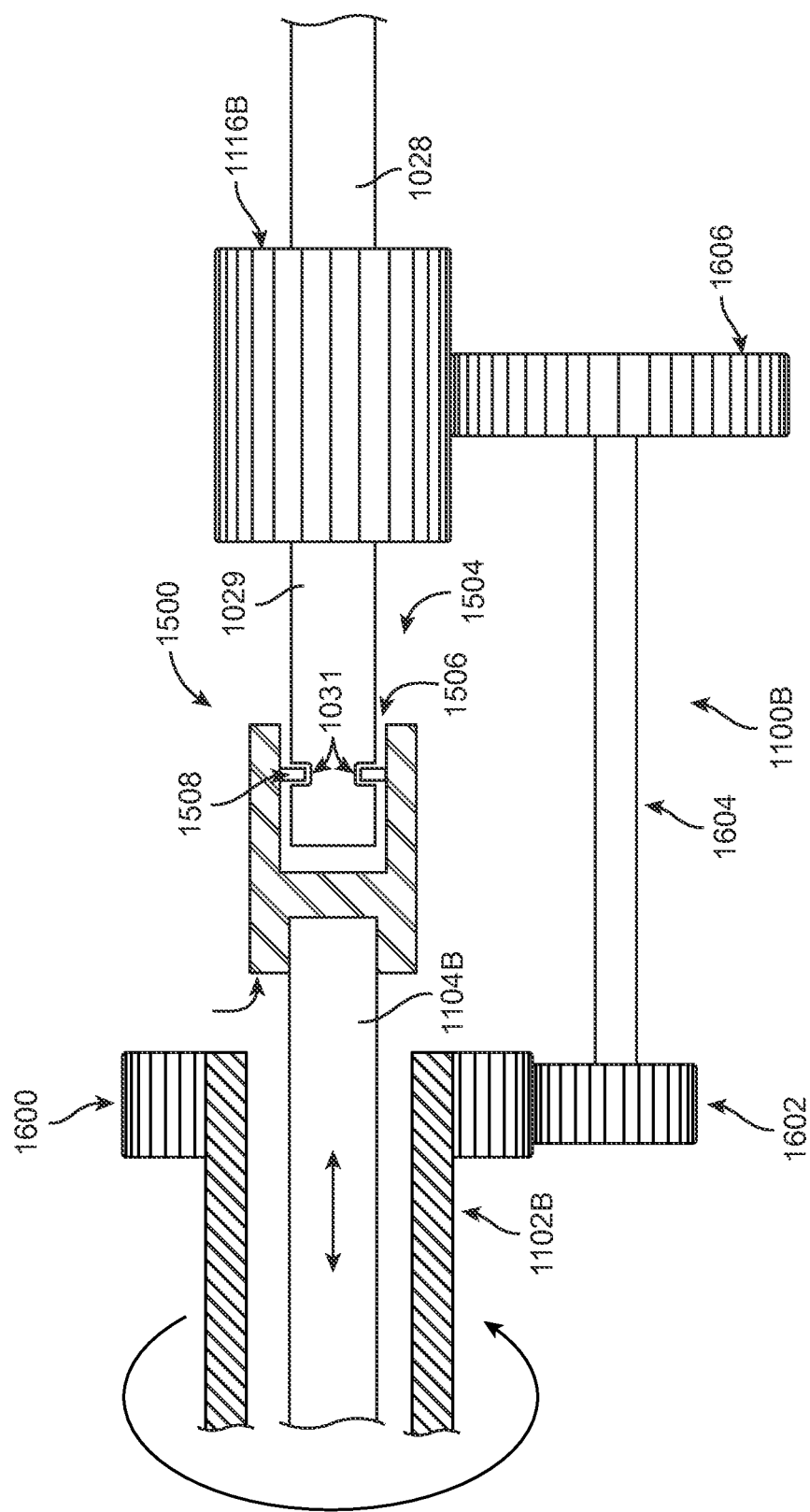
FIG. 8 is a partial cross-sectional view of a connection mechanism connecting coaxial rotational and translational shafts with a cutting mechanism.

The tissue removal device 1002 may include a drive system for transferring the translational movements of the translational shaft 1104B to the inner tubular member 1028 and for transmitting the rotational movement of the rotational shaft 1102B to the inner tubular member 1028. For example, FIG. 8 illustrates a further embodiment of a drive system, identified with the reference numeral 1100B. Components of the drive system 1100B that are similar to the drive systems 1100 and 1100A shown in FIGS. 2 and 5 are identified with the same reference numeral, except that the letter "B" has been added thereto. The drive system 1100B is configured to transfer the translational energy from translational shaft 1104B and the rotational energy from the rotational shaft 1102B (FIG. 7) to the inner tubular member 1028.

For transmitting the translational energy from the translational shaft 1104B to the inner tubular member 1028, the system 1100B includes a connector 1500 which includes a proximal end 1502 fixed to the distal end of the translational shaft 1104B. The proximal end 1502 may be fixed to the translational shaft 1104B with any known type of connector, including, for example but without limitation, glue, interference fit, threaded fastener, etc. As such, the connector 1500 translates with the translational shaft 1104B.

The distal end 1504 of the connector 1500 includes a recess 1506 configured to receive the proximal end 1029 of the inner tubular member 1028. The recess 1506 is configured to have an inner dimension so as to provide clearance relative to the outer surface of the proximal end 1029, which may include a circumferential groove 1031. The recess 1506 may include an inner circumferential projection 1508 configured to extend into the groove 1031. The connector 1500 may be made from a deflectable material, e.g., material that can elastically deflect sufficiently to allow the projection 1508 to deflect radially outwardly as the proximal end 1029 of the inner tubular member 1028 is inserted into the recess 1506 such that the projections 1508 may pass over the proximal tip and then engage the groove 1031. In this engaged state, as the translational shaft 1104B translates proximally and distally, the inner tubular member 1028 also translates proximally and distally.

In order to transfer the rotational energy of the rotational shaft 1102B to the inner tubular member 1028, the system 1100B may also include a coaxial drive gear 1600. The drive gear 1600 may be meshed with a driven gear 1602 mounted to a drive shaft 1604, which may be supported by the housing 1007 (FIG. 1) by bearings (not shown). A further gear 1606 may be mounted to the shaft 1604, and meshed with a gear 1116B fixedly coupled to the inner tubular member 1028.

As such, rotational energy from the distal end of the rotational shaft 1102B is transferred through the drive gear 1600 to the driven gear 1602, through the drive shaft 1604, to the gear 1606, then to the gear 1116B, and thus to the inner tubular member 1028. As described above, the gear 1116B is elongated, allowing the driven gear 1116B to move axially relative to the gear 1606 while remaining meshed with the gear 1606. As such, the inner tubular member 1028 may be driven both translationally by the translational shaft 1104B and rotationally by the rotational shaft 1102B.

The surgical system 100 depicted in FIG. 1 may be used in a variety of different ways and in a variety of contexts. In some embodiments, a method for use comprises insertion of the access device 104 within an orifice of the body or an incision in the body. In this case, the access device 104 is inserted through the cervix and into the uterine cavity. The access device 104 is connected to a fluid supply 106 to introduce a distension media into the body. In this case, the distension media distends the uterine cavity to improve visualization the flaccid organ. In some embodiments, the fluid supply is configured to detect pressure within the body (for example, the uterine cavity) and to maintain a specific pressure.

To remove tissue from the body, for example the uterine body, the surgeon may insert a tissue removal device 1002 into the access device 104. The tissue removal device 1002 is advanced to the distal end of the access device 104 and into the body. The tissue removal device 1002 is connected to a vacuum source 122, and fluid from within the body starts to flow through the tissue removal device 1002 while inflow fluid flows within the working channel of the access device 104 and around the tissue removal device 1002 and into the body. The tissue removal device 1002 is connected to one or more drive shafts 1102, 1102A, 1102B, 1104, 1104B, which are driven by one or more motors 1202, 1220, 1202A, 1202B, 1220B. By activating the motor(s), the drive shaft(s) drive the inner tubular member 1028 within the tissue removal device 1002 to cut tissue within the body, in this case the uterine cavity.

Figure 9A:
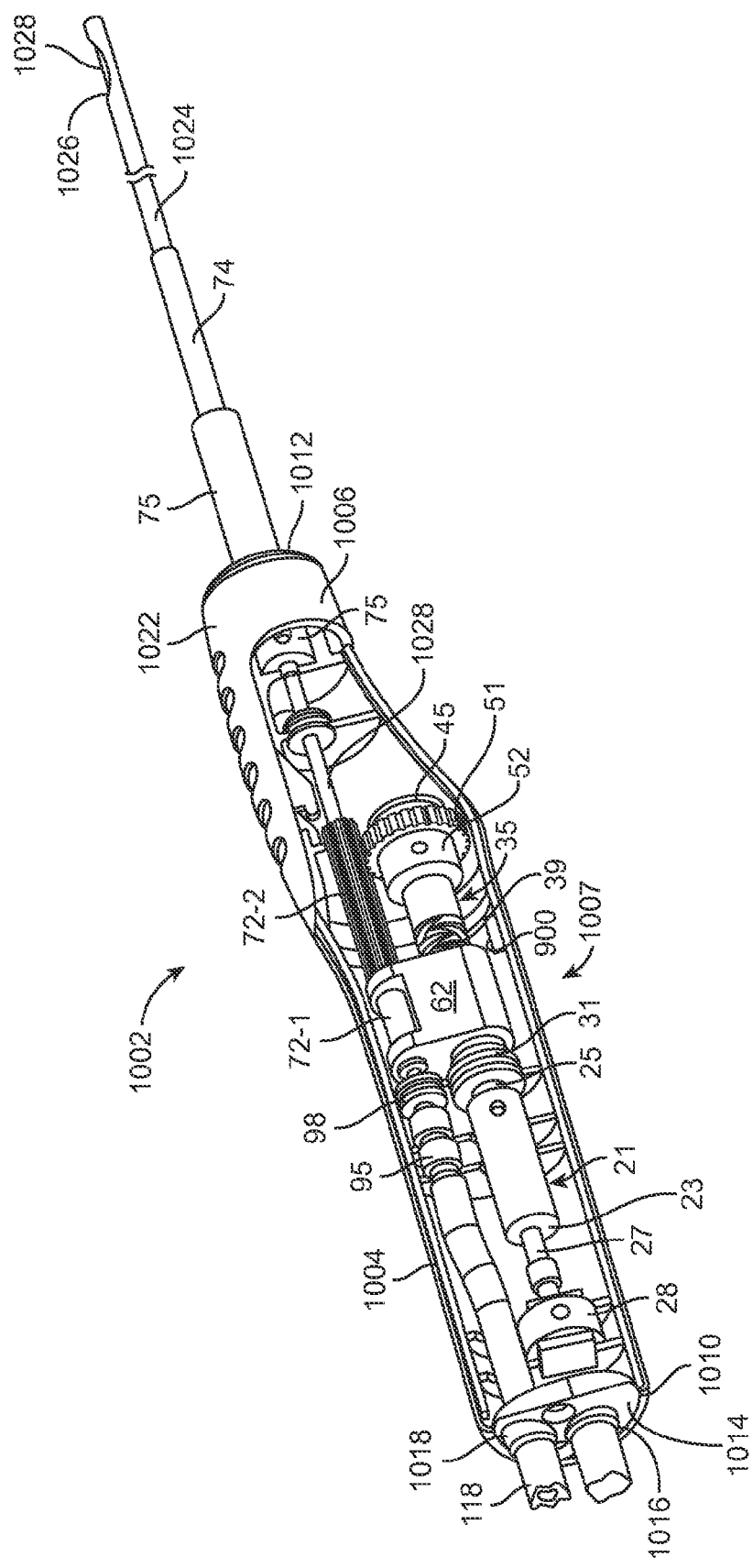
FIGS. 9(a) and 9(b) are perspective and exploded views, respectively, of the components of a tissue removal device.
Figure 9B:
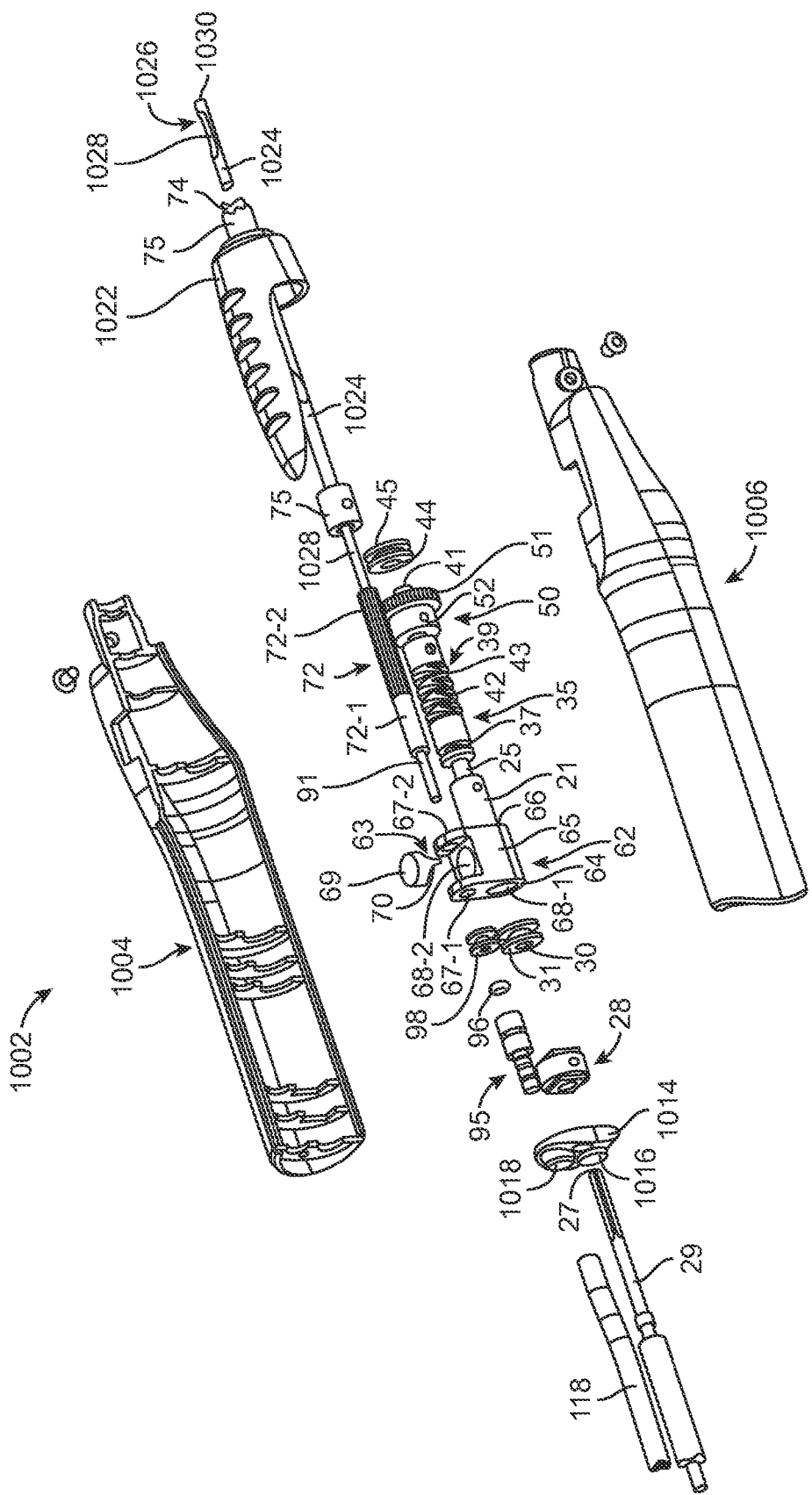

Referring now to FIGS. 9(*a*) and 9(*b*), an embodiment of the tissue removal device 1002 may be seen in greater detail. Many of the components of the tissue removal device 1002 depicted in FIGS. 1, 9(*a*), and 9(*b*) may be similar to the components of the tissue removal device disclosed in U.S. patent application Ser. No. 12/432,647, previously incorporated herein by reference. Thus, further details of the tissue removal device 1002 may be found in U.S. patent application Ser. No. 12/432,647. Device 1002 may include an internal drive shaft 21 adapted for rotation about its longitudinal axis. Shaft 21, which may be an elongated unitary structure made of a suitably rigid metal or polymer, may be shaped to include a proximal end 23 and a distal end 25. Proximal end 23 of shaft 21 may be coaxially mounted over and fixed to the distal end 27 of an external drive shaft 29, so that the rotation of the internal drive shaft 21 is mechanically coupled to the rotation or the external drive shaft 29. The external drive shaft 29 may a rotatable output shaft of the motor (not shown) disposed within the motor drive assembly unit 110 shown in FIG. 1, wherein the distal end of the external drive shaft 29 is inserted through a retainer 28 mounted in housing 1007. Distal end 25 of shaft 21 may be inserted through an opening 30 in an annular bushing 31.

The embodiment depicted in FIGS. 9(*a*) and 9(*b*) includes a single external drive shaft 29, which may be configured to rotate only.

Device 1002 may further comprise a translation drive shaft 35 adapted for rotation about its longitudinal axis. Shaft 35, which may be an elongated unitary structure made of a suitably rigid metal or polymer, may be shaped to include a proximal end 37, an intermediate portion 39, and a distal end 41. Proximal end 37 of shaft 35 may be coaxially mounted over and fixed to the distal end 25 of internal drive shaft 21. In this manner, the rotation of shaft 35 may be mechanically coupled, through the internal drive shaft 21, to the rotation of the external drive shaft 29. Intermediate portion 39 may be shaped to include a double helical portion comprising a right-handed threaded helical channel 42 and a left-handed threaded helical channel 43. Helical channels 42 and 43 may have identical or different pitches. Helical channels 42 and 43 may be smoothly blended together at their respective ends to form a continuous groove so that there may be a smooth transition from one helical channel to the other. Distal end 41 of shaft 35 may be appropriately dimensioned to be received within an opening 44 in an annular bushing 45. It should be noted that, although shaft 35 is adapted for rotation, shaft 35 is translationally stationary.

Device 1002 may further comprise a gear assembly 50 adapted for rotation about its longitudinal axis. Gear assembly 50, which may be an elongated unitary structure made of a suitably rigid metal or polymer, may be shaped to include a distal spur gear 51 and a proximal tube portion 52. Gear assembly 50 may be coaxially mounted over intermediate portion 39 of shaft 35 in an area between the double helical portion and distal end 41, and gear assembly 50 may be fixed to shaft 35 using a pin inserted radially through tube portion 52 and into an opening provided in shaft 35. In this manner, the rotation of spur gear 51 may be mechanically coupled to the rotation of shaft 35.

Device 1002 may further comprise an oscillating translation assembly, which may include a carriage 62 and a channel engagement member 63. Carriage 62, which may be a unitary structure made of a suitably rigid metal or polymer, may be shaped to include a proximal portion 64, an intermediate portion 65, and a distal portion 66. The tops of proximal portion 64 and distal portion 66 may extend beyond the top of intermediate portion 65 and may be shaped to include loops 67-1 and 67-2, respectively, loops 67-1 and 67-2 being aligned with one another. A longitudinal bore 68-1 may be provided near the bottom of carriage 62, bore 68-1 being appropriately dimensioned to coaxially receive intermediate portion 39 of shaft 35 while permitting intermediate portion 39 to rotate freely therewithin. Channel engagement member 63, which may be a unitary structure made of a suitably rigid metal or polymer, may be shaped to include a base 69 and a pawl 70. Base 69 may be disposed in an opening 68-2 that may extend downwardly from the top of intermediate portion 65 into communication with the longitudinal bore 68-1, with pawl 70 traveling within the double helical portion of shaft 35. In this manner, as shaft 35 rotates, pawl 70 may continuously travel back and forth through the double helical portion of shaft 35, thereby causing carriage 62 to oscillate translationally. As can be appreciated, the speed at which carriage 62 oscillates translationally may be varied, for example, by varying the translational length of the double helical portion of shaft 35, the angles of the helical channels 42 and 43, the rotational speed of shaft 29, etc. It may be desirable to operate the device 1002 so that carriage 62 oscillates translationally at about 2.8 cycles per second.

Device 1002 may further comprise a shaft 72 adapted for rotation about its longitudinal axis. Shaft 72, which may be an elongated, unitary, tubular structure made of a suitably rigid metal or polymer, may be shaped to include a proximal portion 72-1 and a distal portion 72-2. Proximal portion 72-1 may be inserted through loops 67-1 and 67-2 of carriage 62 and may freely rotate relative to loops 67-1 and 67-2. Distal portion 72-2 may be in the form of an elongated pinion gear. Distal portion 72-2 may be engaged with spur gear 51 of gear assembly 50 so that the rotation of spur gear 51 causes the rotation of shaft 72. Distal portion 72-2 may be elongated so that it may maintain engagement with spur gear 51 even as distal portion 72-2 moves translationally relative to spur gear 51. The speed at which distal portion 72-2 rotates (and, therefore, the speed at which shaft 72 rotates) may be the same as or different than the speed at which spur gear 51 rotates, depending, for example, on the relative diameters of the two gears. The ratio of the rotational speeds of the two gears 51 and 72-2 is inversely proportional to the ratio of the diameters of the two gears 51 and 72-2. Consequently, by appropriately dimensioning spur gear 51 and distal portion 72-2, a desired rotational speed may be achieved, even where the rotational speed of the external drive shaft 29 is fixed. For example, in the embodiment shown, distal portion 72-2 has a diameter that is one-fourth the diameter of spur gear 51 and, therefore, rotates four times as fast as gear 51. Therefore, if the external drive shaft 29 has a speed of rotation of about 1500 rpm, gear 51 would rotate at 1500 rpm, and distal portion 72-2 would rotate at 6000 rpm. As can be appreciated, the rotational speed of distal portion 72-2 does not depend on the interaction of the carriage 62 with the double helical portion of shaft 35. Consequently, distal portion 72-2 may attain higher or lower rotational speeds than would be possible based on the requirements of a desired translational speed. Notwithstanding the above, shaft 72 is translationally coupled to carriage 62. Consequently, as carriage 62 oscillates translationally, so does shaft 72.

An intermediate length of the inner tubular member 1028 may be coaxially received within shaft 72 and may be fixedly coupled to shaft 72 for translational and rotational movement therewith. The proximal end 91 of the inner tubular member 1028 may be slideably mounted within a vacuum tube connector 95, which may, in turn, be coupled to the vacuum tube 118 inserted through lumen 1018 of cap 1014. An O-ring 96 may be mounted within connector 95 to maintain a good seal with the inner tubular member 1028. An annular bushing 98 mounted within housing 1007 may be used to receive the inner tubular member 1028 and to maintain its alignment.

Rather than having a double helical portion, the translational shaft 35 may alternatively have a single helix. In this embodiment, when the carriage 62 reaches the distal end or the proximal end of the single helix, the rotation of the translational shaft 35 may be reversed in order to axially translate the carriage 62 towards the opposite end of the helix. In order to reverse the rotation of the translational shaft 35, the motor (disposed within the unit 110 and not shown) coupled to the external drive shaft 29 may be reversed. When the motor is reversed, the drive shaft 29 changes from clockwise rotation to counter-clockwise rotation, or vice versa. A motor control switch 900 positioned within the housing 1007 adjacent to the carriage 62, and is operatively coupled to the motor through motor control circuitry, such that actuation of the switch 900 causes the motor to reverse direction. Additional details of the motor control switch 900 are discussed below.

In a further alternative, only one of the helical grooves 42 or 43 of the double helical portion may be utilized. That is, the translational shaft 35 and the carriage 62 may be configured such that the pawl 70 of the channel engagement member 63 engages with only one of the helical grooves 42 or 43. In this embodiment, when the carriage 62 reaches the distal end or the proximal end of the helical portion, the rotation of the translational shaft 35 may be reversed in order to axially translate the carriage 62 towards the opposite end of the helical portion. In order to reverse the rotation of the translational shaft 35, the motor output (disposed within the unit 110 and not shown) and, thus, the rotational direction of the external drive shaft 29 is reversed.

In particular, the motor control switch 900 is actuated when the carriage 62 and the inner tubular member 1028 are in their distal-most positions, and the tissue resection window 1026 is closed. Positioning the switch 900 so that contact is made when the inner tubular member 1028 is in, or very close to, its distal-most position ensures the tissue resection window 1026 is closed prior to the change in translational direction of the inner member 1028 to the proximal direction, and may also ensure that the resection window 1026 is closed when the motor turns off. Rotation of the translational shaft 35 is reversed by reversing the rotation of the external drive shaft 29, and rotation of the external drive shaft 29 is reversed by reversing the motor coupled to the proximal end of the external drive shaft 29. Thus, actuating the motor control switch 900 reverses the motor and causes the external drive shaft 29 to change from clockwise rotation to counter-clockwise rotation, or vice versa. In the illustrated embodiment, the switch 900 is actuated by the carriage 62 pushing the switch 900 distally.

Upon actuation of the motor control switch 900, the motor reverses, the external drive shaft 29 changes its direction of rotation, the translational shaft 35 changes rotational direction, and the carriage 62 moves proximally relative to the translational shaft 35. When the carriage 62 moves proximally, the switch 900 is released. The switch 900 is configured to automatically return to its original position upon release. The original position of the switch 900 is depicted in FIG. 9(*a*). For example, the motor control switch 900 may include a spring, or the like, for automatically returning the switch 900 to the original position.

When the carriage 62 reaches the proximal end of the helical portion of the translational shaft 35, the motor automatically reverses again, thereby changing the rotational direction of the respective external drive shaft 29 and translational drive shaft 35, and causing the carriage 62 to move in the distal direction. This may be accomplished by employing a second motor control switch (not shown) positioned within the removal device housing 1007 adjacent to the proximal end of the translational shaft 35, so that the second switch is actuated when the carriage 62 reaches the proximal end of the helical portion of the translational shaft 35. In this manner, the motor output shaft 29 reverses direction each time one of the motor control switches is actuated at the respective distal-most and proximal-most movement of the carriage 62.

Alternatively, one or more encoders (not shown) may be employed to determine the timing for reversing the motor. In particular, since the length of the resection window 1026 is known, the motor control circuitry may be configured for causing the motor to reverse when the inner tubular member 1028 has translated axially through a distance equal to the length of the resection window 1026, based on input supplied by the one or more encoders. For example, based on the number of windings in the helix on the translational shaft 35, the inner tubular member 1028 axially translates through a distance equal to the length of the resection window 1026 when the translational shaft 35 or the external drive shaft 29 rotates a predetermined number of times. Thus, the encoder(s) may be configured for tracking the number of revolutions of the translational shaft 35 or the external drive shaft 29. Based on input from the encoder(s), the motor control circuitry may be configured for causing the motor to reverse when the translational shaft 35 or the external drive shaft 29 has rotated the predetermined number of times.

In one embodiment, the tissue removal device 1002 may include a combination of motor control switches and encoders configured for causing the motor to reverse when the carriage 62 reaches one of the ends of the helix. In particular, the tissue removal device 1002 may include a switch 900 configured for causing the motor to reverse when the carriage 62 is at the distal-most or proximal-most position, and may also include motor control circuitry having one or more encoders for tracking the number of revolutions of the external drive shaft 29 to determine when to again reverse the direction of the motor. The motor control circuitry may receive input from the one or more encoders that tracks the number of revolutions of the translational shaft 35 or the drive shaft 29, and, based on the input from the encoder(s), may cause the motor to reverse when the translational shaft 35 or the drive shaft 29 has rotated a predetermined number of times since the switch 900 was actuated at the opposite end of the translational shaft 35. For example, in the embodiment shown in FIGS. 9(*a*) and 9(*b*), the motor control switch 900 may be configured for causing the motor to reverse when the carriage 62 is in the distal-most position, and the motor control circuitry may be configured for causing the motor to reverse when the carriage 62 is in the proximal-most position, as determined based on a number of revolutions of the translational shaft 35 or the drive shaft 29. The switch 900 may be more accurate than an encoder for detecting the position of the inner tubular member 1028. Thus, in this embodiment, a switch 900 may be used to accurately detect when the inner tubular member 1028 is in its distal-most position. When the inner tubular member 1028 is in its distal-most position, the resection window 1026 is closed, and it may be advantageous to ensure that the resection window 1026 is closed prior to reversing the motor or turning the motor off, as discussed in more detail below.

In addition to being configured for causing the motor to reverse, thereby changing the translational direction of the inner tubular member 1028, the motor control switch 900 may also be used to ensure that the inner tubular member 1028 is in, or very close to, its distal-most position and the resection window 1026 is in the closed position when the motor turns off. By ensuring the resection window 1026 is closed when the motor turns off, unnecessary removal of distension fluid from the body cavity through the resection window is prevented. The tissue removal system may include a second motor control switch external to the housing 1007. Both the internal and the external motor control switches may be operatively coupled to motor control circuitry (not shown) configured such that actuation of the second, external motor control switch causes the motor to turn on. In the embodiment shown in FIG. 1, this second motor control switch takes the form of a foot pedal 1036. When a user pushes the foot pedal 1036, the motor turns on. Continued pressure on the foot pedal 1036 keeps the motor on. When the user releases the foot pedal 1036, the motor control circuitry may be configured such that the motor may continue to operate until the carriage 62 is in the distal-most position, which indicates that the inner tubular member 1028 is in the distal-most, or closed position. The motor control switch 900 within the housing 1007 may be employed to ensure that the carriage 62 is in the distal-most position. Thus, the motor control circuitry is configured such that only when the carriage 62 contacts the switch 900, and the foot pedal 1036 has been released, does the motor turn off.

In summary, when the foot pedal 1036 is actuated, actuation of the motor control switch 900 causes the motor to reverse. However, when the foot pedal 1036 is not actuated, actuation of the motor control switch 900 causes the motor to turn off.

In some embodiments, the portion of the motor control circuitry that includes the motor control switch 900 a normally open circuit. When the switch 900 is actuated, the circuit is closed, and a signal is sent to the motor, which causes the motor to reverse or turn off. Because the tissue removal device 1002 is used with a distension fluid that may enter the interior of the housing 1007, the switch 900 may be immersed with the distension fluid. Thus, the motor control circuitry may include an impedance monitor to distinguish actual contact by the carriage 62 from an electrical "short" caused by the distention fluid. Based on input from the impedance monitor, the motor control circuitry may be configured for causing the motor to reverse or turn off only when the impedance is below a predetermined level that indicates the switch has been actuated. For example, if saline is used as the distension fluid, the motor control circuitry may be configured for causing the motor to reverse or turn off only when the input from the impedance monitor indicates that the impedance is lower than the impedance of saline.

Figure 10A:
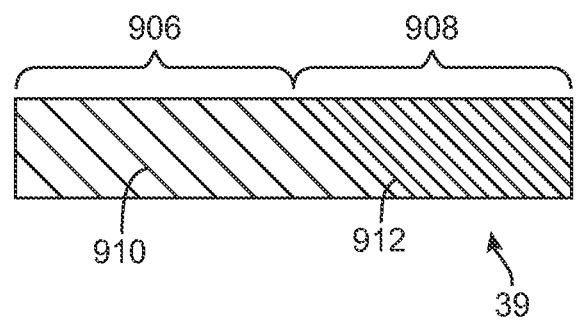
FIGS. 10(a)-10(c) are embodiments of helical portions comprising variable pitches.
Figure 10B:
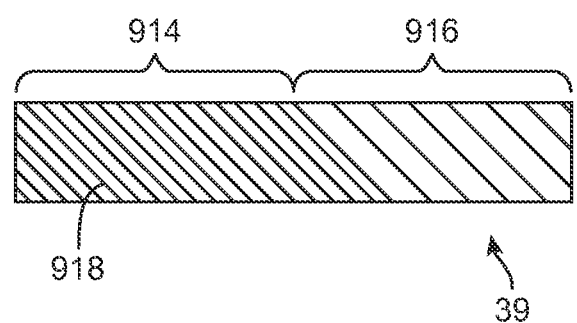

The translational shaft 35 may include a variable pitch helix, as depicted in FIGS. 10(*a*)-10(*c*). That is, the helix 39 on the translational shaft 35 may include portions where the windings are closer together and portions where the windings are farther apart. With such a variable pitch, the speed of the axial translation of the inner tubular member 1028 varies depending on the distance between the windings. When the windings are farther apart, and the shaft 35 is rotated at the same speed, the inner tubular member 1028 translates quickly because the channel engagement member 63 travels through fewer windings during axial movement. In contrast, when the windings are closer together, the inner tubular member 1028 translates slower because the channel engagement member 63 travels through more winding during axial movement.

In one embodiment, shown in FIG. 10(*a*), the windings 910 on the proximal portion 906 of the helix 39 are farther apart so that the axial movement of the cutter 1028 is faster at the beginning of the resection window 1026. Such a variable pitch helix may optimize the performance of the system. For example, the momentum caused by relatively quick action at the beginning of the resection window 1026 may facilitate cutting the tissue. However, if the motion of the cutter 1028 is too fast at the beginning of the resection window 1026, the tissue may move out of the resection window 1026 before being cut. The windings 912 on the distal portion 908 of the helix 39 may be closer together in order to slow the axial movement of the cutter 1028 to facilitate cutting and deceleration.

Figure 10C:
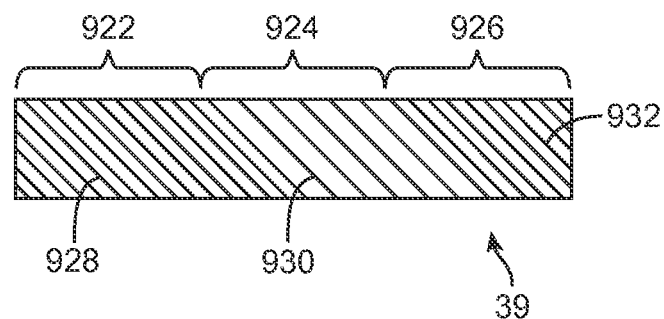

Alternatively, as shown in FIG. 10(*b*), the windings 918 in the proximal portion 914 of the helix 39 may be closer together, and the windings 920 in the distal portion 916 of the helix 39 may be farther apart. In yet another embodiment, shown in FIG. 10(c) the windings 928 and 932 in both the distal and proximal ends 922 and 926 of the helix 39 may be closer together, and the windings 930 in the central portion 924 of the helix 39 may be farther apart, or vice versa.

Conditional language, such as, among others, "can," "could," "might," or "may," unless specifically stated otherwise, or otherwise understood within the context as used, is generally intended to convey that some embodiments include, while other embodiments do not include, some features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although the embodiments of the inventions have been disclosed and described in the context of some preferred embodiments and examples, it will be understood by those skilled in the art that the present inventions extend beyond the specifically disclosed embodiments to other alternative embodiments and/or uses of the inventions and obvious modifications and equivalents thereof, and that other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Accordingly, it should be understood that various features and aspects of the disclosed embodiments can be combine with or substituted for one another in order to form varying modes of the disclosed inventions. For all of the embodiments described herein, the steps of the methods need not be performed sequentially, unless specifically set forth in the claim(s) as requiring a sequential order. Thus, it is intended that the scope of the disclosed inventions should not be limited by the particular disclosed embodiments, but are limited only as set forth in the following claims.

What is claimed is:

1. A tissue removal system, comprising:
    an outer tubular member having a closed distal end and a tissue resection window proximal to the distal end;
    an inner tubular member disposed within the outer tubular member and configured to translate axially relative to the outer tubular member, wherein the tissue resection window is closed-off by the inner tubular member when the inner tubular member is in a distal position relative to the outer tubular member;
    a housing coupled to a proximal end of the outer tubular member;
    a reversible motor operatively coupled to the inner tubular member, such that activation of the motor causes the inner tubular member to translate axially relative to the outer tubular member;
    a motor control switch disposed within the housing, wherein a structure coupled to the inner tubular member contacts the motor control switch when the inner tubular member translates axially to the distal position relative to the housing; and
    motor control circuitry operatively coupled to the motor control switch and the motor, the motor control circuitry including an impedance monitor that monitors an impedance of a circuit including the motor control switch and detects when the motor control switch is contacted by detecting a change in impedance not caused by a presence of saline in the circuit, and wherein the motor control circuitry is configured for causing the motor to reverse when the impedance monitor detects that the motor control switch is contacted.

2. The tissue removal system of claim 1, the motor comprising a rotatable output shaft, and the system further comprising a translational shaft operatively coupled to the respective motor output shaft and inner tubular member, wherein the translational shaft comprises a helical groove, and wherein rotation of the output shaft causes rotation of the translational shaft.

3. The tissue removal system of claim 2, the structure coupled to the inner tubular member comprising a carriage configured to engage the helical groove on the translational shaft and to oscillate axially relative to the translational shaft when the translational shaft is rotating, such that the inner tubular member oscillates axially with the carriage.

4. The tissue removal system of claim 2, the helical groove comprising a variable pitch, wherein windings in a first portion of the helical groove are closer together than windings in a second portion of the helical groove.

5. The tissue removal system of claim 1, further comprising a second motor control switch operatively coupled with the motor that is contacted by the structure when the inner tubular member translates axially to a proximal position relative to the housing in which the tissue resection window is not blocked by the inner tubular member, wherein contacting the second motor control switch reverses the motor.

6. A tissue removal system, comprising:
    an outer tubular member having a closed distal end and a tissue resection window proximal to the distal end;
    an inner tubular member disposed within the outer tubular member and configured to translate axially relative to the outer tubular member, wherein the tissue resection window is closed-off by the inner tubular member when the inner tubular member is in a distal position relative to the outer tubular member;
    a housing coupled to a proximal end of the outer tubular member, wherein a proximal end of the inner tubular member is disposed within, and configured to reciprocate axially relative to, the housing;
    a motor operatively coupled to the inner tubular member, such that activation of the motor causes the inner tubular member to reciprocate axially relative to the outer tubular member;
    a first motor control switch disposed within the housing, wherein a structure coupled to the inner tubular member contacts the first motor control switch when the inner tubular member reaches the distal position relative to the housing; and
    a second motor control switch disposed external to the housing and configured for being actuated by a user, wherein the first and second motor control switches are operatively coupled to motor control circuitry that is operatively coupled to the motor, the motor control circuitry including an impedance monitor that monitors impedance of a circuit including the motor control switch and detects when the first motor control switch is contacted by detecting a change in impedance not caused by a presence of saline in the circuit, the motor control circuitry configured to deactivate the motor when the impedance monitor detects that the first motor control switch is contacted when the second motor control switch is not actuated.

7. The tissue removal system of claim 6, wherein the second motor control switch comprises a foot pedal.

8. The tissue removal system of claim 6, the motor comprising a rotatable output shaft, and the system further comprising
a translational shaft coupled to and between the motor output shaft and the inner tubular member, the translational shaft comprising a helical groove, wherein rotation of the output shaft causes rotation of the translational shaft.

9. The tissue removal system of claim 8, the structure coupled to the inner tubular member comprising a carriage configured to engage the helical groove on the translational shaft and to oscillate axially relative to the translational shaft when the translational shaft is rotating, such that the inner tubular member oscillates axially with the carriage.

10. The tissue removal system of claim 6, the motor comprising a reversible motor with a rotatable output shaft,
the system further comprising a translational shaft operatively coupled to the respective motor output shaft and inner tubular member,
wherein the respective motor output shaft and translational shaft are configured such that rotation of the motor output shaft in a first direction causes the inner tubular member to translate axially in a distal direction, and wherein rotation of the output shaft in a second direction opposite to the first direction causes the inner tubular member to translate axially in a proximal direction.

11. A tissue removal system, comprising:
an outer tubular member having a closed distal end and a tissue resection window proximal to the distal end;
an inner tubular member disposed within the outer tubular member and configured to rotate and translate axially relative to the outer tubular member, wherein the tissue resection window is closed-off by the inner tubular member when the inner tubular member is in a distal position relative to the outer tubular member;
a housing coupled to a proximal end of the outer tubular member, wherein a proximal end of the inner tubular member is disposed within, and configured to rotate and translate axially relative to, the housing;
a reversible motor comprising a rotatable output shaft operatively coupled to the inner tubular member, such that rotation of the output shaft in a first direction causes the inner tubular member to translate axially in a distal direction, and wherein rotation of the output shaft in a second direction opposite to the first direction causes the inner tubular member to translate axially in a proximal direction, wherein the inner tubular member automatically oscillates axially relative to the outer tubular member during operation of the tissue removal system;
an internal motor control switch disposed within the housing and operatively coupled to the motor, wherein the internal motor control switch is contacted when the inner tubular member is in the distal position relative to the housing; and
an external motor control switch disposed external to the housing and operatively coupled to the motor,
wherein the internal and external motor control switches are operatively coupled to motor control circuitry that is operatively coupled to the motor, the motor control circuitry including an impedance monitor that monitors impedance of a circuit including the first motor control switch and detects when the internal motor control switch is contacted by detecting a change in impedance not caused by a presence of saline in the circuit, and
wherein the motor control circuitry is configured to cause the motor to turn off or the motor output shaft to reverse direction of rotation, depending on whether the external motor control switch is actuated when the impedance monitor detects that the internal motor control switch is contacted.

12. The tissue removal system of claim 11, wherein the motor control circuitry is configured such that, when the external motor control switch is actuated, contacting the internal motor control switch causes the motor output shaft to change direction of rotation.

13. The tissue removal system of claim 11, wherein the motor control circuitry is configured such that, when the external motor control switch is not actuated, contacting the internal motor control switch causes the motor to turn off.

14. The tissue removal system of claim 11, wherein the external motor control switch comprises a foot pedal.

15. The tissue removal system of claim 11, further comprising a translational shaft coupled to and between the motor output shaft and the inner tubular member, the translational shaft comprising a helical groove, wherein rotation of the output shaft causes rotation of the translational shaft.

16. The tissue removal system of claim 15, the structure coupled to the inner tubular member comprising a carriage configured to engage the helical groove on the translational shaft, and to oscillate axially relative to the translational shaft when the translational shaft is rotating, such that the inner tubular member oscillates axially with, and rotates relative to, the carriage.

17. The tissue removal system of claim 15, the helical groove comprising a variable pitch, wherein windings in a first portion of the helical groove are closer together than windings in a second portion of the helical groove.

* * * * *